US011568467B2

United States Patent
Jiang et al.

(10) Patent No.: US 11,568,467 B2
(45) Date of Patent: Jan. 31, 2023

(54) LEVERAGING FEATURE ENGINEERING TO BOOST PLACEMENT PREDICTABILITY FOR SEED PRODUCT SELECTION AND RECOMMENDATION BY FIELD

(71) Applicant: CLIMATE LLC, San Francisco, CA (US)

(72) Inventors: Dongming Jiang, Chesterfield, MO (US); Herbert Ssegane, Maryland Heights, MO (US); Shilpa Sood, Chesterfield, MO (US); Xiao Yang, Chesterfield, MO (US); Xuefei Wang, Creve Coeur, MO (US)

(73) Assignee: CLIMATE LLC, San Francisco, CA (US)

( * ) Notice: Subject to any disclaimer, the term of this patent is extended or adjusted under 35 U.S.C. 154(b) by 193 days.

(21) Appl. No.: 16/845,052

(22) Filed: Apr. 9, 2020

(65) Prior Publication Data

US 2020/0327603 A1 Oct. 15, 2020

Related U.S. Application Data

(60) Provisional application No. 62/832,148, filed on Apr. 10, 2019.

(51) Int. Cl.
G06Q 30/06 (2012.01)
G06Q 50/02 (2012.01)
(Continued)

(52) U.S. Cl.
CPC ..... *G06Q 30/0631* (2013.01); *G06F 16/2462* (2019.01); *G06N 7/005* (2013.01);
(Continued)

(58) Field of Classification Search
None
See application file for complete search history.

(56) References Cited

U.S. PATENT DOCUMENTS

| 6,505,146 | B1 | 1/2003 | Blackmer |
| 7,047,133 | B1 * | 5/2006 | Dyer ...................... G06Q 10/04 |
| | | | 702/5 |

(Continued)

FOREIGN PATENT DOCUMENTS

| CA | 3049258 | | 7/2018 | |
| CA | 3049258 | A1 * | 7/2018 | ............... A01H 3/00 |

(Continued)

OTHER PUBLICATIONS

Shahhossenie et al. "Forecasting Corn Yield With Machine Learning Ensembles" (2000) (https://www.frontiersin.org/articles/10.3389/fpls.2020.01120/full) (Year: 2000).*

(Continued)

*Primary Examiner* — Sujay Koneru
(74) *Attorney, Agent, or Firm* — Harness, Dickey & Pierce, P.L.C.

(57) ABSTRACT

An example computer-implemented method includes receiving a plurality of agricultural data records including yield properties of products grown in fields and raw field features of the fields. The method also includes transforming the raw field features into distinct feature classes that characterize key features affecting yield of the one or more products, and generating, using data from the plurality of agricultural data records and the distinct feature classes, genomic-by-environmental relationships between one or more products, yield properties of the one or more products, and field features associated with the one or more products. Further, the method includes generating, based at least in part on the genomic-by-environmental relationships, predicted yield performance for a set of products associated (Continued)

with one or more target environments, generating product recommendations for the one or more target environments based on the predicted yield performance for the set of products, and providing one or more instructions configured to cause display of the product recommendations.

11 Claims, 19 Drawing Sheets

(51) Int. Cl.
*G06N 20/00* (2019.01)
*G06N 7/00* (2006.01)
*G06F 16/2458* (2019.01)
*G16B 20/00* (2019.01)
*A01B 79/00* (2006.01)

(52) U.S. Cl.
CPC .............. *G06N 20/00* (2019.01); *G06Q 50/02* (2013.01); *G16B 20/00* (2019.02); *A01B 79/005* (2013.01)

(56) References Cited

U.S. PATENT DOCUMENTS

| | | | |
|---|---|---|---|
| 10,028,451 | B2 | 7/2018 | Rowan et al. |
| 10,251,347 | B2 | 4/2019 | Xu et al. |
| 10,338,272 | B2 | 7/2019 | Xiang et al. |
| 10,586,158 | B2 | 3/2020 | Chen et al. |
| 2005/0234691 | A1 | 10/2005 | Singh et al. |
| 2009/0099776 | A1 | 4/2009 | Kapadi et al. |
| 2014/0090431 | A1* | 4/2014 | Blotsky ............... C05F 11/08 510/109 |
| 2015/0066932 | A1 | 3/2015 | Stuber et al. |
| 2015/0124054 | A1 | 5/2015 | Darr et al. |
| 2016/0073573 | A1* | 3/2016 | Ethington ........... A01B 79/005 705/7.36 |
| 2016/0202227 | A1 | 7/2016 | Mathur et al. |
| 2017/0122889 | A1* | 5/2017 | Weindorf ............... G01N 33/24 |
| 2017/0169523 | A1* | 6/2017 | Xu ....................... A01C 21/00 |
| 2018/0018517 | A1* | 1/2018 | Zhong ................. G06K 9/6215 |
| 2018/0020622 | A1* | 1/2018 | Richt .................... G06Q 10/04 703/6 |
| 2018/0070527 | A1* | 3/2018 | Richt .................. A01B 79/005 |
| 2018/0168094 | A1* | 6/2018 | Koch .................... A01C 7/102 |
| 2018/0211156 | A1* | 7/2018 | Guan ................... G06N 3/0454 |
| 2019/0139158 | A1 | 5/2019 | Reich et al. |
| 2019/0360962 | A1* | 11/2019 | Kusano ................ G01N 27/414 |
| 2020/0042890 | A1* | 2/2020 | Merrill .................. G06Q 50/02 |
| 2020/0096434 | A1* | 3/2020 | Deran ................. G01N 15/147 |
| 2020/0134486 | A1 | 4/2020 | Jiang |
| 2020/0154629 | A1* | 5/2020 | Holoubek .............. A01C 7/102 |

FOREIGN PATENT DOCUMENTS

| | | |
|---|---|---|
| CN | 108291265 | 7/2018 |
| WO | WO 2017/013462 | 1/2017 |
| WO | WO2017/214445 | 12/2017 |
| WO | WO 2018/208722 | 11/2018 |

OTHER PUBLICATIONS

International Bureau, "International Preliminary Report on Patentability", in Application No. PCT/US2020/027562, dated Oct. 21, 2021, 8 pages.
International Bureau, "International Preliminary Report on Patentability" in application No. PCT/US19/057812, dated May 6, 2021, 10 pages.
Current Claims in application No. PCT/US19/057812, dated May 2021, 5 pages.
Canada Patent Office, "Office Action", in Application No. 3,092,808, dated Oct. 18, 2021, 4 pages.
Canada Claims, in Application No. 3,092,808, dated Oct. 18, 2021, 7 pages.
The International Searching Authority, "Search Report:" in application No. PCT/US20/27562, dated Jul. 2, 2020, 16 pages.
Current Claims in application No. PCT/US20/27562, dated Jul. 2020, 5 pages.
International Searching Authority, "Search Report" in application No. PCT/US 19/57812, dated Feb. 3, 2020, 17 pages.
Current Claims in application No. PCT/US 19/57812, dated Feb. 2020, 5 pages.

* cited by examiner

FIG. 2
(a)
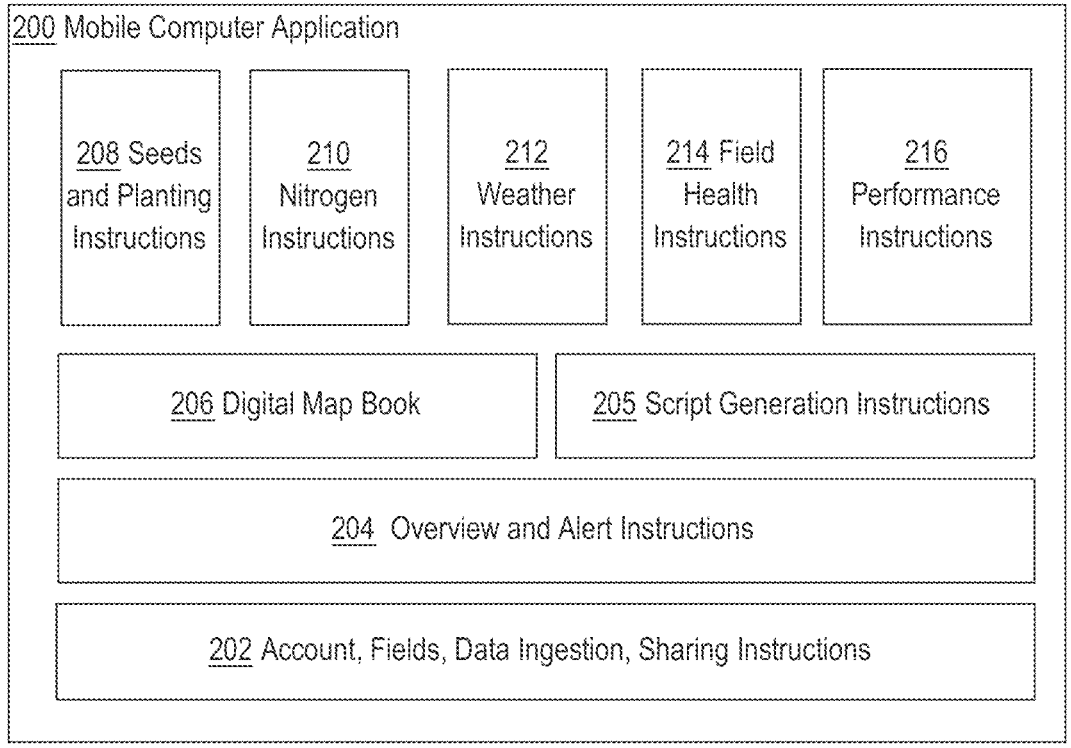
(b)
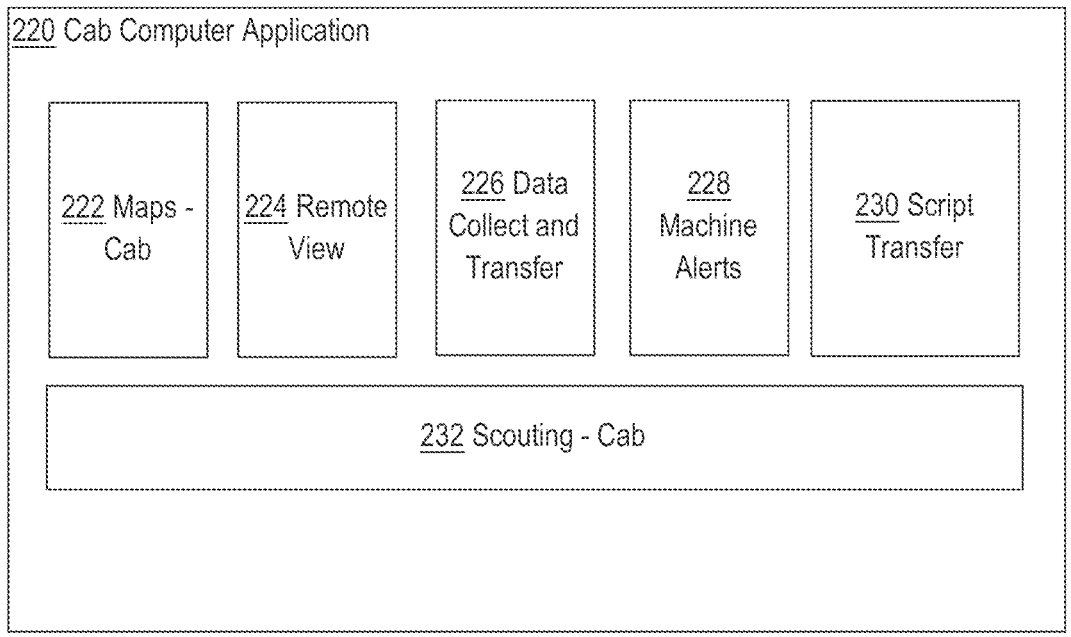

FIG. 5

Data Manager

| Nitrogen | Planting | Practices | Soil |

Planting 1(4 Fields)
Crop Corn Product
Plant Date: 2016-04-12
iLU 112 | Pop: 34000
[Edit] [Apply]

Planting 2(0 Fields)
Crop Corn Product
Plant Date: 2016-04-15
iLU 83 | Pop: 34000
[Edit] [Apply]

Planting 3(0 Fields)
Crop Corn Product
Plant Date: 2016-04-13
iLU 83 | Pop: 34000
[Edit] [Apply]

Planting 4(1 Fields)
Crop Corn Product
Plant Date: 2016-04-13
iLU 112 | Pop: 34000
[Edit] [Apply]

[+] Add New Planting Plan

| | CROP | PLANTED ACRES | PRODUCT | RELATIVE MATURITY | TARGET YIELD | POPULATION(AVG) | PLA |
|---|---|---|---|---|---|---|---|
| ☐ Select All | | | | | | | |
| ☐ Ames, IA 1 Corn \| 100 \| Boone, IA | Corn | --- | DMC82-M | 112 | 160 | 34000 | Apr |
| ☐ Austin, MN 1 Corn \| 100 \| Fredricks, MN | Corn | --- | DMC82-M | 114 | 160 | 36000 | Apr |
| ☐ Boone, IN 1 Corn \| 100 \| Boone, IA | Corn | --- | DMC82-M | 112 | 150 | 34000 | Apr |
| ☐ Champaign 1 Corn \| 100 \| Champaign, IL | Corn | --- | --- | 112 | 200 | 34000 | Apr |
| ☐ E Nebraska 1 Corn \| 100 \| Burl, NE | Corn | --- | --- | 112 | 160 | 34000 | Apr |

705 Receive One or More Agricultural Data Records of Crop Seed Data and Field Data Containing Seed and Yield Properties of Seeds and Field Geo-location Data for Fields where Seeds Planted

710 Receive Location Information for One or More Target Fields

715 Normalization: Generate Dataset of Seed Properties for One or More Seeds Containing Representative Yield Value and Environmental Classification of the One or More Seeds

720 Generate Dataset of Success Probability Scores for One or More Seeds where Success Probability Score is Probability of Successful Yield that is Higher than Average Yield based on Dataset of Seed Properties and Location Information for One or More Target Fields

725 Generate Target Success Yield Group of a Subset of the One or More Seeds using a Successful Yield Threshold to Identify the Subset of the Seed(s) that have Success Probability Scores Above Successful Yield Threshold

730 Display Target Success Yield Group with Yield Values for each Seed in the Subset

LEVERAGING FEATURE ENGINEERING TO BOOST PLACEMENT PREDICTABILITY FOR SEED PRODUCT SELECTION AND RECOMMENDATION BY FIELD

RELATED APPLICATIONS

This application claims the benefit under 35 U.S.C. § 119(e) of provisional application No. 62/832,148 filed Apr. 10, 2019, the entire contents of which is hereby incorporated by reference for all purposes as if fully set forth herein.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2015-2019 The Climate Corporation.

FIELD OF THE DISCLOSURE

One technical field of the present disclosure is computer-implemented decision support systems for agriculture, particularly in relation to seed selection and planting strategies. Another technical field is computer systems that are programmed to use genetic characteristics of seeds and agricultural features of fields to generate predictive and comparison yield data for one or more fields. A further technical field is computer systems that are programmed to recommend selection and placement of seeds in one or more unique target fields to help improve yield quantities and consistency.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

A successful harvest depends on many factors including seed selection, soil fertilization, irrigation, pest control, and management practices, which each contributes to the growth rate of plants, for instance, corn or soybean plants. One of the most important agricultural management factors is choosing which seeds to plant on target fields. Seed varieties or hybrids range from seeds suited for short growth seasons to longer growth seasons, hotter or colder temperatures, dryer or wetter climates, and different seeds suited for specific soil compositions. Achieving optimal performance for a specific seed hybrid or variety depends on whether the field conditions align with the optimal growing conditions for the specific seed. For example, a specific soybean variety may be rated to produce a specific amount of yield for a grower, however, if the field conditions do not match the optimal conditions used to rate the specific soybean variety, it is unlikely that the soybean variety will consistently meet the yield expectations for the grower.

Once a set of seeds, hybrids, or varieties are chosen for planting, a grower must then determine a planting strategy. Planting strategies include determining the amount and placement of each of the chosen products. Strategies for determining amount and placement may dictate whether harvest yield meets expectations. For example, planting seeds that have similar strengths and vulnerabilities may result in a good yield if conditions are favorable. However, if conditions fluctuate, such as receiving less than expected rainfall or experiencing higher than normal temperatures, then overall yield for similar seeds may be diminished. A diversified planting strategy may be preferred to overcome unforeseen environmental fluctuations.

Techniques described herein help alleviate some of these issues and help growers determine what seeds to plant in which fields.

BRIEF DESCRIPTION OF THE DRAWINGS

FIG. 2 illustrates two views of an example logical organization of sets of instructions in main memory when an example mobile application is loaded for execution.

FIG. 5 depicts an example embodiment of a timeline view for data entry.

FIG. 6 depicts an example embodiment of a spreadsheet view for data entry.

FIG. 7 depicts an example flowchart for generating a target success yield group of seeds identified for optimal yield performance on target fields based on agricultural data records of the seeds and geo-location data associated with the target fields.

DETAILED DESCRIPTION

Figure 1:
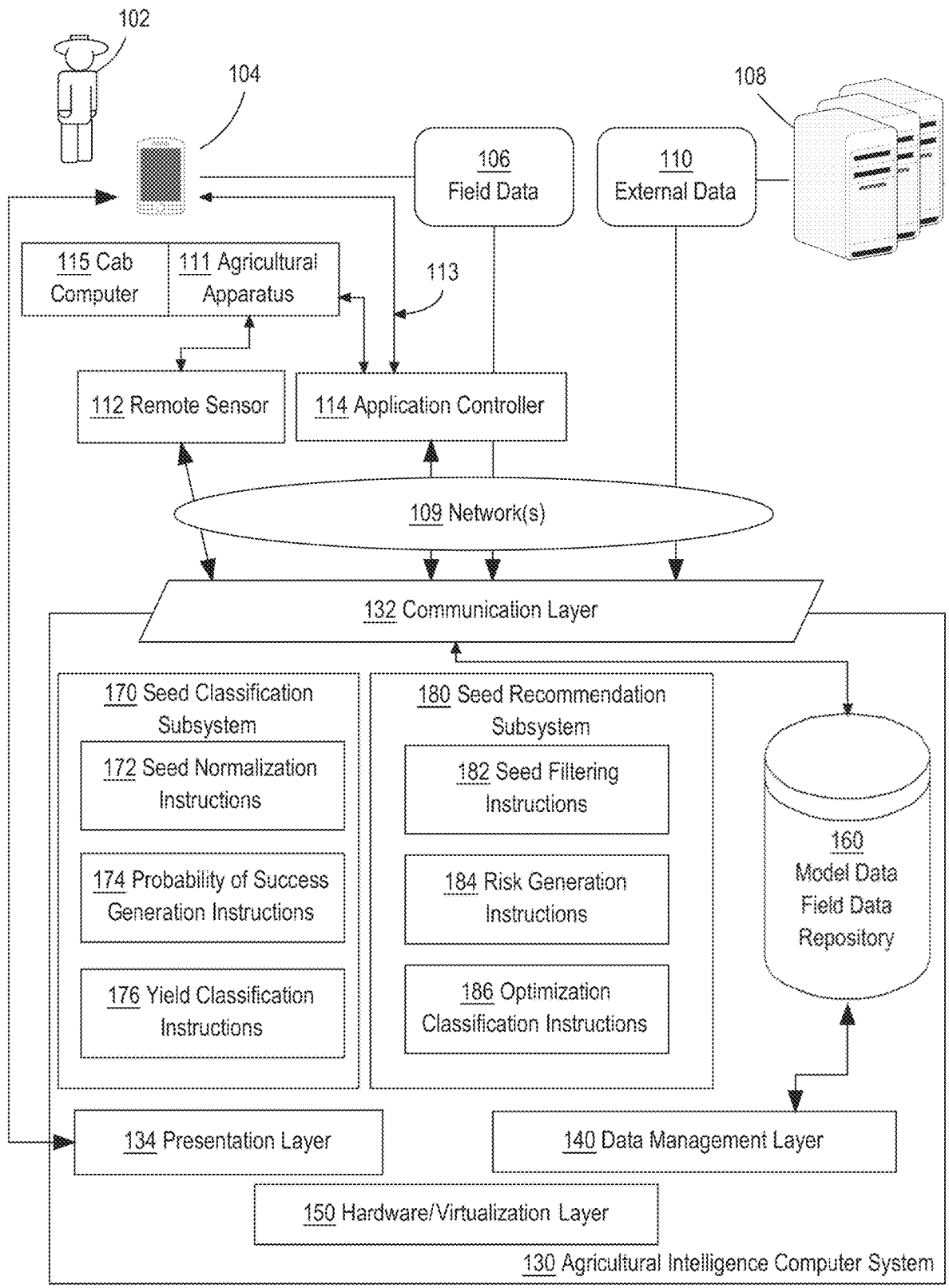
FIG. 1 illustrates an example computer system that is configured to perform the functions described herein, shown in a field environment with other apparatus with which the system may interoperate.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:

1. GENERAL OVERVIEW
2. EXAMPLE AGRICULTURAL INTELLIGENCE COMPUTER SYSTEM
    2.1. STRUCTURAL OVERVIEW
    2.2. APPLICATION PROGRAM OVERVIEW
    2.3. DATA INGEST TO THE COMPUTER SYSTEM
    2.4. PROCESS OVERVIEW—AGRONOMIC MODEL TRAINING
    2.5. SEED CLASSIFICATION SUBSYSTEM
    2.6. SEED RECOMMENDATION SUBSYSTEM
    2.7. IMPLEMENTATION EXAMPLE—HARDWARE OVERVIEW
3. FUNCTIONAL OVERVIEW—GENERATE AND DISPLAY TARGET SUCCESS YIELD GROUP OF SEEDS
    3.1. DATA INPUT
    3.2. AGRICULTURAL DATA PROCESSING
    3.3. PRESENT TARGET SUCCESS YIELD GROUP
4. FUNCTIONAL OVERVIEW—GENERATE AND DISPLAY TARGET SEEDS FOR PLANTING
    4.1. DATA INPUT
    4.2. SEED SELECTION
    4.3. GENERATE RISK VALUES FOR SEEDS
    4.4. GENERATE DATASET OF TARGET SEEDS
    4.5. SEED PORTFOLIO ANALYSIS
    4.6. PRESENT SET OF TARGET SEEDS
5. FUNCTIONAL OVERVIEW—GENERATE AND DISPLAY YIELD IMPROVEMENT RECOMMENDATION BY FIELD
    5.1. DATA INPUT
    5.2. DATA IMPUTATION
    5.3. DETERMINE PREDICTED YIELD PERFORMANCE
    5.4. SEED OPTIMIZATION AND RECOMMENDATION GENERATION
    5.5. VALIDATE AND ADJUST MODELS
6. FUNCTIONAL OVERVIEW—EMBODIMENT INCLUDING FEATURE ENGINEERING TO ENHANCE DATA FOR RECOMMENDATION MODELING
    6.1 RAW FEATURES AND FEATURE CLASSIFICATION
    6.2 PREPARE DATA

1. General Overview

A computer system and a computer-implemented method are disclosed herein for generating a set of target success yield group of agricultural products, such as seeds, hybrids, and/or varieties, that have a high probability of a successful yield on one or more target fields. In an embodiment, a target success yield group of seeds may be generated using a server computer system that is configured to receive, over a digital data communication network, one or more agricultural data records that represent crop seed data describing seed and yield properties of one or more seeds and first field geo-location data for one or more agricultural fields where the one or more seeds were planted. The server computer system then receives second geo-locations data for one or more target fields where seeds are to be planted.

The server computer system includes seed normalization instructions configured to generate a dataset of seed properties that describe a representative yield value and an environmental classification for each seed from the one or more agricultural data records. Probability of success generation instructions on the server computer system are configured to then generate a dataset of success probability scores that describe the probability of a successful yield on the one or more target fields. A successful yield may be defined as an estimated yield value for a specific seed for an environmental classification that exceeds the average yield for the same environmental classification by a specific yield amount. The probability of success values for each seed are based upon the dataset of seed properties and the second geo-location data for the one or more target fields.

The server computer system includes yield classification instructions configured to generate a target success yield group made up of a subset of the one or more seeds and the probability of success values associated with each of the subset of the one or more seeds. Generation of the target success yield group is based upon the dataset of success probability scores for each seed and a configured successful yield threshold, where seeds are added to the target success yield group if the probability of success value for a seed exceeds the successful yield threshold.

The server computer system is configured to cause display, on a display device communicatively coupled to the server computer system, of the target success yield group and yield values associated with each seed in the target success yield group.

In an embodiment, the target success yield group (or another set of seeds and fields) may be used to generate a set of target seeds selected for planting on the one or more target fields. The server computer system is configured to receive the target success yield group of candidate seeds that may be candidates for planting on the one or more target fields. Included in the target success yield group is the one or more seeds, the probability of success values associated with each of the one or more seeds that describe a probability of a successful yield, and historical agricultural data associated with each of the one or more seeds. The server computer then receives property information related to the one or more target fields.

Seed filtering instructions within the server computer system are configured to select a subset of the hybrid seeds or seed varieties that have probability of success values greater than a target probability filtering threshold. The server computer system includes seed normalization instructions configured to generate representative yield values for seeds in the subset of the one or more seeds based on the historical agricultural data.

The server computer system includes risk generation instructions configured to generate a dataset of risk values for the subset of the one or more seeds. The dataset of risk values describes risk associated with each seed based on the historical agricultural data. The server computer system includes optimization classification instructions configured to generate a dataset of target seeds for planting on the one or more target fields based on the dataset of risk values, the representative yield values for the subset of the one or more seeds, and the one or more properties for the one or more target fields. The dataset of target seeds includes target seeds that have the representative yield values that meet a specific target threshold for a range of risk values from the dataset of risk values across the one or more target fields.

The server computer system is configured to display, on the display device communicatively coupled to the server computer system, the dataset of target seeds including the representative yield values and risk values from the dataset of risk values associated with each target seed in the dataset of target seeds and the one or more target fields.

In another embodiment, a computer-implemented method comprises receiving, over a digital data communication network at a server computer system, agricultural data records comprising a first set of yield properties for a first set of seeds grown in a first set of environments, and further receiving, over the digital data communication network, genetic feature data related to a second set of seeds, wherein the second set of seeds includes the first set of seeds. The method also includes generating, using the server computer system, a second set of yield properties for the second set of seeds associated with a second set of environments by applying the genetic feature data to the agricultural data records. In this example, the second set of yield properties fills data gaps from the first set of yield properties. The server computer system can then be used to determine predicted yield performance on one or more target fields for one or more seeds, such as a third set of seeds, which may be the same or different from the first and/or second sets of seeds. The predicted yield performance may be based on one or more of an absolute or relative yield values, yield ranking, a probability of success score, and/or other considerations. In one example, the server computer determines predicted yield performance for the second set of seeds associated with the second set of environments by applying the imputed yield properties, and generates yield improvement recommendations based on the predicted yield performance for the second set of seeds. The method may also include causing display, on a display device communicatively coupled to the server computer system, of the yield improvement recommendations.

In another embodiment, a computer-implemented method comprises receiving, over a digital data communication network at a server computer system, agricultural data records comprising a set of yield properties for a set of seeds grown in a set of environments, wherein the set of yield properties includes yield properties generated by applying genetic relationship data between the seeds. The method further includes receiving, over the digital data communication network, feature data for one or more target fields where seeds are to be planted. The server computer system may then be used to generate seed recommendations for the one or more target fields based on the set of yield properties and the feature data. And, the method may also include causing display, on a display device communicatively coupled to the server computer system, of the seed recommendations.

A further embodiment utilizes feature engineering to enhance feature data that is used to generate field-specific seed recommendations for target fields or environments. Feature engineering techniques disclosed herein include identifying from raw field features (e.g., environment, weather, soil, topography, hydrology, and/or management-related field features) key features that are significant drivers of yield, and performing feature classification on the key features to transform continuous features into categorical features. In this embodiment, a computer system uses the resulting key categorical features in recommendation modelling to enhance results as compared to using raw, continuous features. More particularly, the computer system receives agricultural data records, such as crop seed data, yield properties, and associated field features, and performs feature engineering techniques to identify key field features and classify or characterize key field feature data into classes or categories. The computer system is configured to use the resulting processed field feature data in association with the seed data and yield properties to characterize interactions between genetic, environmental, and/or management features. The computer system is further configured to utilize the genetic/environmental/management interactions to predict yield performance and generate agricultural product recommendations to help improve yield. These feature engineering techniques help to deconvolute complex higher-order feature interactions and improve field-specific product recommendations.

2. Example Agricultural Intelligence Computer System 2.1 Structural Overview

FIG. 1 illustrates an example computer system that is configured to perform the functions described herein, shown in a field environment with other apparatus with which the system may interoperate. In one embodiment, a user 102 owns, operates or possesses a field manager computing device 104 in a field location or associated with a field location such as a field intended for agricultural activities or a management location for one or more agricultural fields. The field manager computer device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) or maturity group (MG) of planted seed(s), seed population), (e) fertilizer data (for example, nutrient type (Nitrogen, Phosphorous, Potassium), application type, application date, amount, source, method), (f) chemical application data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, rainfall rate, predicted rainfall, water runoff rate region, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of data that might otherwise be obtained from third party sources, such as weather data. In some embodiments, an external data server 108 may actually be incorporated within the system 130.

An agricultural apparatus 111 may have one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, aerial vehicles including unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is example of such a network that can be installed in combines, harvesters, sprayers, and cultivators. Application controller 114 is communicatively coupled to agricultural intelligence computer system 130 via the network(s) 109 and is programmed or configured to receive one or more scripts that are used to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, Calif., is used. Sensor data may consist of the same type of information as field data 106. In some embodiments, remote sensors 112 may not be fixed to an agricultural apparatus 111 but may be remotely located in the field and may communicate with network 109.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a graphical screen display, such as a color display, that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, distributed databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGRESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user may specify identification data by accessing field identification data (provided as shape files or in a similar format) from the U. S. Department of Agriculture Farm Service Agency or other source via the user device and providing such field identification data to the agricultural intelligence computer system.

In an example embodiment, the agricultural intelligence computer system 130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 5:
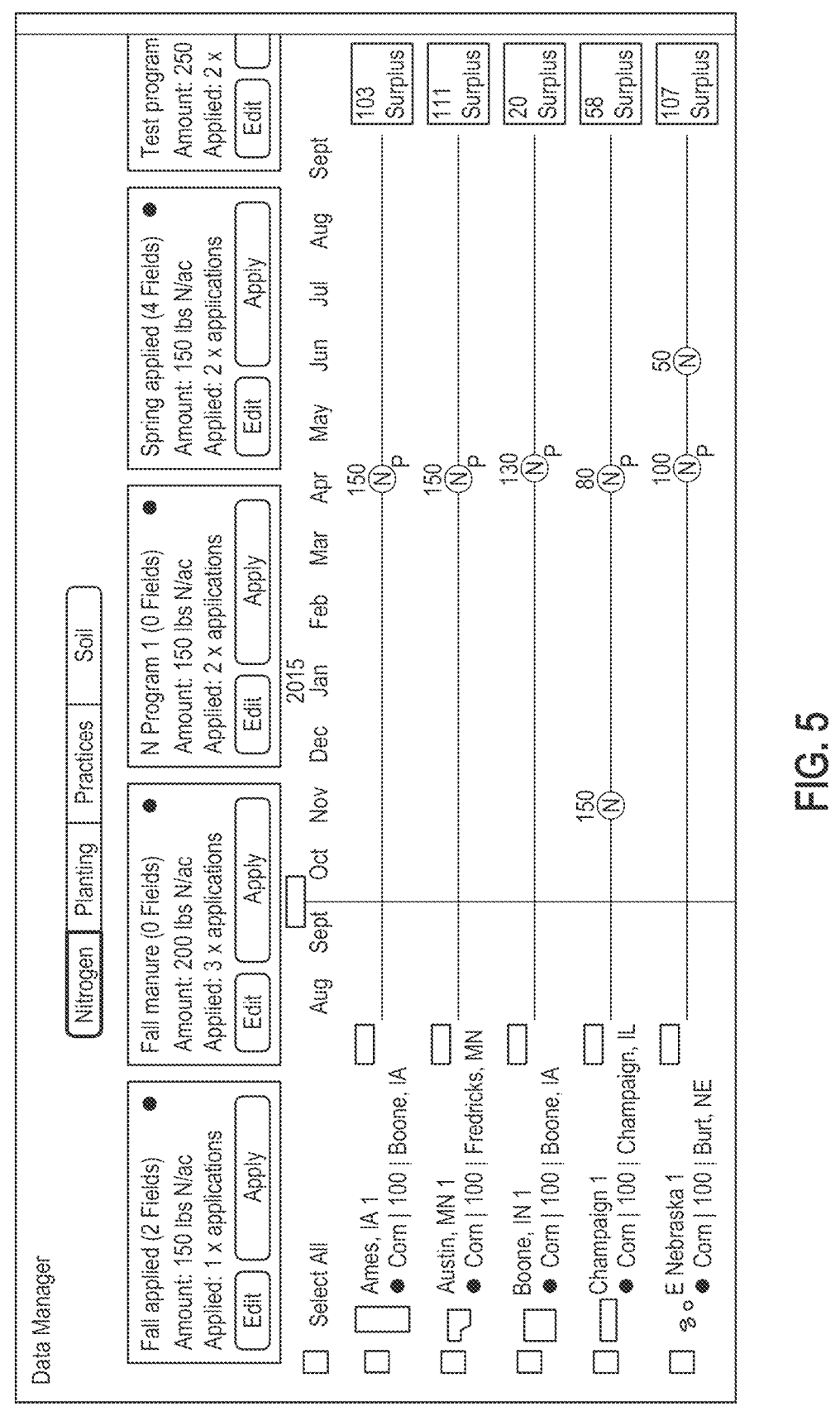

FIG. 5 depicts an example embodiment of a timeline view for data entry. Using the display depicted in FIG. 5, a user computer can input a selection of a particular field and a particular date for the addition of event. Events depicted at the top of the timeline may include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 5, the top two timelines have the "Spring applied" program selected, which includes an application of 150 lbs. N/ac in early April. The data manager may provide an interface for editing a program. In an embodiment, when a particular program is edited, each field that has selected the particular program is edited. For example, in FIG. 5, if the "Spring applied" program is edited to reduce the application of nitrogen to 130 lbs. N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 5, the interface may update to indicate that the "Spring applied" program is no longer being applied to the top field. While the nitrogen application in early April may remain, updates to the "Spring applied" program would not alter the April application of nitrogen.

FIG. 6 depicts an example embodiment of a spreadsheet view for data entry. Using the display depicted in FIG. 6, a user can create and edit information for one or more fields. The data manager may include spreadsheets for inputting information with respect to Nitrogen, Planting, Practices, and Soil as depicted in FIG. 6. To edit a particular entry, a user computer may select the particular entry in the spreadsheet and update the values. For example, FIG. 6 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored or calculated output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In an embodiment, a seed classification subsystem 170 contains specially configured logic, including, but not limited to, seed normalization instructions 172, probability of success or predicted yield performance generation instructions 174, and yield classification instructions 176 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. In an embodiment, a seed recommendation subsystem 180 contains specially configured logic, including, but not limited to, seed filtering instructions 182, risk generation instructions 184, and optimization classification instructions 186 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. For example, the seed normalization instructions 172 may comprise a set of pages in RAM that contain instructions which when executed cause performing the target identification functions that are described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each of seed normalization instructions 172, probability of success or predicted yield performance generation instructions 174, yield classification instructions 176, seed filtering instructions 182, risk generation instructions 184, and optimization classification instructions 186 also may represent one or more files or projects of source code that are digitally stored in a mass storage device such as non-volatile RAM or disk storage, in the agricultural intelligence computer system 130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 130.

Figure 4:
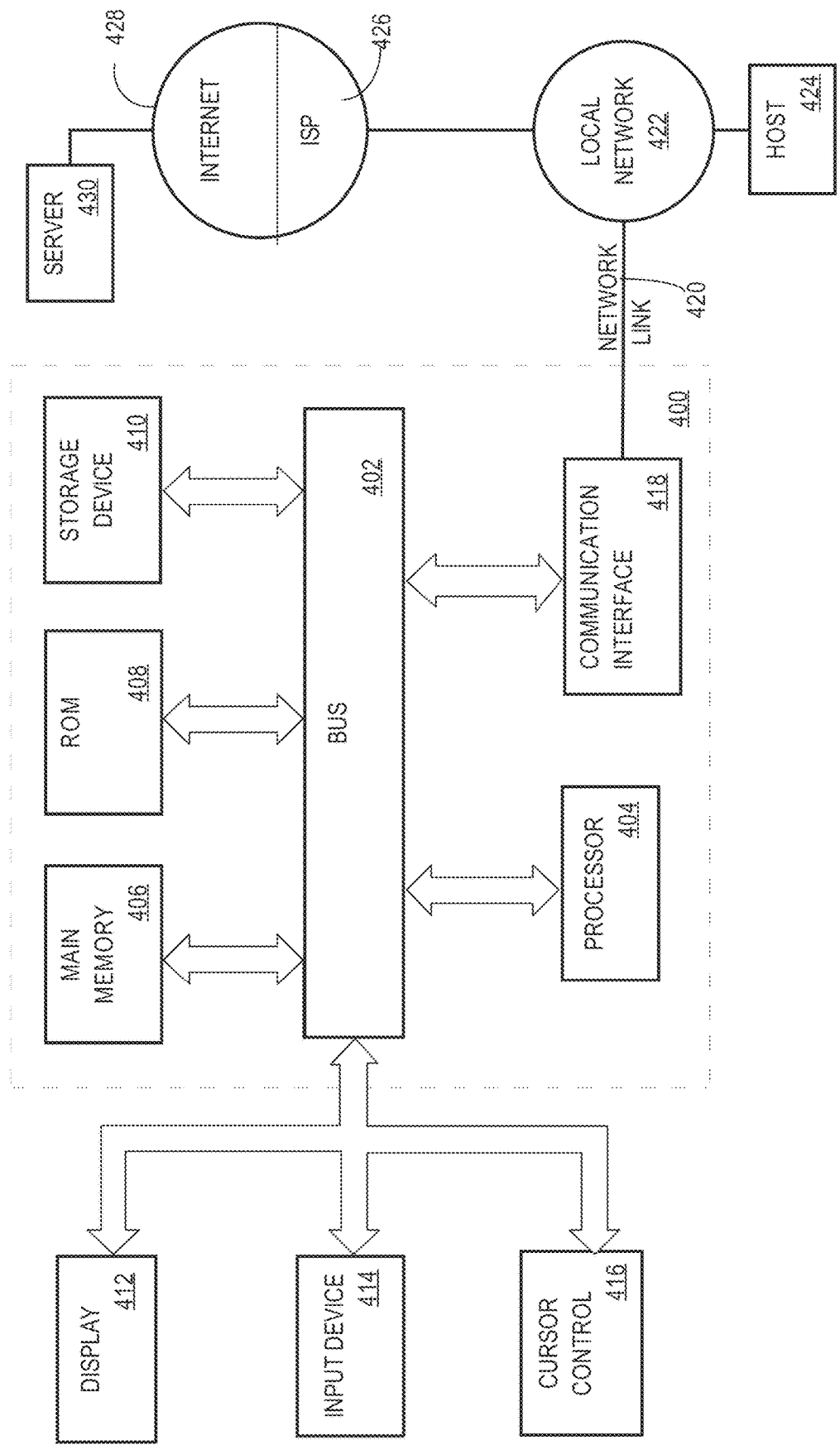
FIG. 4 is a block diagram that illustrates a computer system upon which an embodiment of the disclosure may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system independently and automatically under program control or logical control and direct user interaction is not always required. Field manager computing device 104 broadly represents one or more of a smart phone, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide client-side functionality, via the network to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), WiFi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including, but not limited to, data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114 which include an irrigation sensor and/or irrigation controller. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLI-MATE FIELDVIEW, commercially available from The Climate Corporation, San Francisco, Calif. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account, fields, data ingestion, sharing instructions 202 which are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, e-mail with attachment, external APIs that push data to the mobile application, or instructions that call APIs of external systems to pull data into the mobile application. In one embodiment, mobile computer application 200 comprises a data inbox. In response to receiving a selection of the data inbox, the mobile computer application 200 may display a graphical user interface for manually uploading data files and importing uploaded files to a data manager.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, seed placement, and script creation, including variable rate (VR) script creation, based upon scientific models and empirical data. This enables growers to maximize yield or return on investment through optimized seed purchase, placement and population.

In one embodiment, script generation instructions 205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 200 may display one or more fields broken into management zones, such as the field map data layers created as part of digital map book instructions 206. In one embodiment, the management zones comprise soil zones along with a panel identifying each soil zone and a soil name, texture, drainage for each zone, or other field data. Mobile computer application 200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 200 may make the script available for download in a format readable by an application controller, such as an archived or compressed format. Additionally, and/or alternatively, a script may be sent directly to cab computer 115 from mobile computer application 200 and/or uploaded to one or more data servers and stored for further use.

In one embodiment, nitrogen instructions 210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of fertilizer application zones and/or images generated from subfield soil data, such as data obtained from sensors, at a high spatial resolution (as fine as millimeters or smaller depending on sensor proximity and resolution); upload of existing grower-defined zones; providing a graph of plant nutrient availability and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields and/or zones that have been defined in the system; example data may include nitrogen application data that is the same for many fields and/or zones of the same grower, but such mass data entry applies to the entry of any type of field data into the mobile computer application 200. For example, nitrogen instructions 210 may be programmed to accept definitions of nitrogen application and practices programs and to accept user input specifying to apply those programs across multiple fields. "Nitrogen application programs," in this context, refers to stored, named sets of data that associates: a name, color code or other identifier, one or more dates of application, types of material or product for each of the dates and amounts, method of application or incorporation such as injected or broadcast, and/or amounts or rates of application for each of the dates, crop or hybrid/variety that is the subject of the application, among others. "Nitrogen practices programs," in this context, refer to stored, named sets of data that associates: a practices name; a previous crop; a tillage system; a date of primarily tillage; one or more previous tillage systems that were used; one or more indicators of application type, such as manure, that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for application of other nutrients (such as phosphorus and potassium), application of pesticide, and irrigation programs.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at agricultural intelligence computer system 130 and/or external data server computer 108 and configured to analyze metrics such as yield, yield differential, hybrid/variety, population, SSURGO zone, soil test properties, or elevation, among others. Programmed reports and analysis may include yield variability analysis, treatment effect estimation, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 232 may be programmed to display location-based alerts and information received from the system 130 based on the location of the field manager computing device 104, agricultural apparatus 111, or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, Calif., may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or WiFi-based position or mapping apps that are programmed to determine location based upon nearby WiFi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid/variety selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus; other electromagnetic radiation emitters and reflected electromagnetic radiation detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

In an embodiment, sensors 112 and controllers 114 may comprise weather devices for monitoring weather conditions of fields. For example, the apparatus disclosed in U.S. Provisional Application No. 62/154,207, filed on Apr. 29, 2015, U.S. Provisional Application No. 62/175,160, filed on Jun. 12, 2015, U.S. Provisional Application No. 62/198,060, filed on Jul. 28, 2015, and U.S. Provisional Application No. 62/220,852, filed on Sep. 18, 2015, may be used, and the present disclosure assumes knowledge of those patent disclosures.

2.4. Process Overview-Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, fertilizer recommendations, fungicide recommendations, pesticide recommendations, harvesting recommendations and other crop management recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge or sensor providing weather data at the same or nearby location or an estimate of nitrogen content with a soil sample measurement.

Figure 3:
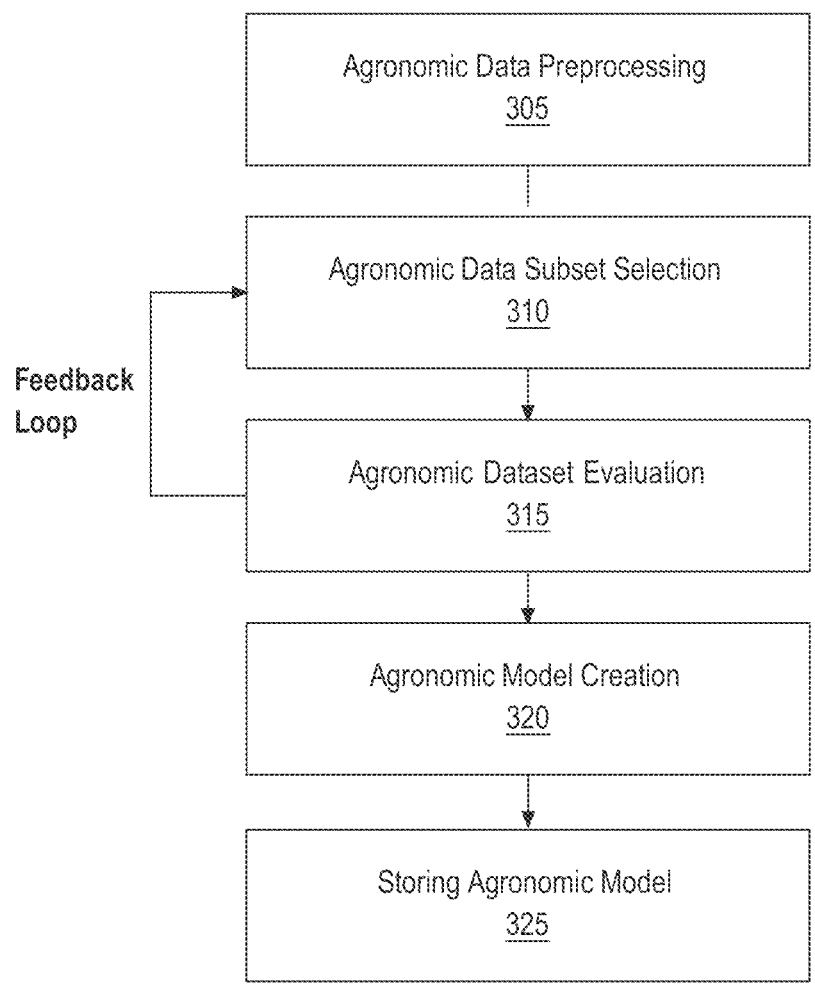
FIG. 3 illustrates a programmed process by which the agricultural intelligence computer system generates one or more preconfigured agronomic models using agronomic data provided by one or more data sources.

FIG. 3 illustrates a programmed process by which the agricultural intelligence computer system generates one or more preconfigured agronomic models using field data provided by one or more data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise, distorting effects, and confounding factors within the agronomic data including measured outliers that could adversely affect received field data values. Embodiments of agronomic data preprocessing may include, but are not limited to, removing data values commonly associated with outlier data values, specific measured data points that are known to unnecessarily skew other data values, data smoothing, aggregation, or sampling techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models' method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared and/or validated using one or more comparison techniques, such as, but not limited to, root mean square error with leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5. Seed Classification Subsystem

In an embodiment, the agricultural intelligence computer system 130, among other components, includes the seed classification subsystem 170. The seed classification subsystem 170 is configured to generate a target success yield group of seeds specifically identified for optimal performance on target fields. As used herein the term "optimal" and related terms (e.g., "optimizing", "optimization", etc.) are broad terms that refer to the "best or most effective" with respect to any outcome, system, data etc. ("universal optimization") as well as improvements that are "better or more effective"("relative optimization"). The target success yield group includes a subset of one or more seeds, an estimated yield forecast for each seed, and a probability of success of exceeding the average estimated yield forecast for similarly classified seeds.

In an embodiment, identifying seeds that will optimally perform on target fields is based on input received by the agricultural intelligence computer system 130 including, but not limited to, agricultural data records for multiple different seeds and geo-location data related to the fields where the agricultural data records were collected. For example, if agricultural data records are received for one-hundred seeds, then the agricultural data records would include growth and yield data for the one-hundred seeds and geo-location data about the fields where the one-hundred seeds were planted. In an embodiment, the agricultural intelligence computer system 130 also receives geo-location and agricultural data for a second set of fields. The second set of fields are the target fields where the grower intends to plant selected seeds. Information about the target fields are particularly relevant for matching specific seeds to the environment of the target fields.

The seed normalization instructions 172 provide instructions to generate a dataset of seed properties that describe representative yield values and environmental classifications that relate to preferred environmental conditions for each of the seeds received by the agricultural intelligence computer system 130. The probability of success generation instructions 174 provide instructions to generate a dataset of success probability scores associated with each of the seeds. The success probability scores describe the probability of a successful yield on the target fields. The yield classification instructions 176 provide instructions to generate a target success yield group of seeds that have been identified for optimal performance on target fields based on the success probability scores associated with each of the seeds.

In an embodiment, the agricultural intelligence computer system 130 is configured to present, via the presentation layer 134, the target success yield group of selected seeds and their normalized yield values and success probability scores.

Seed classification subsystem 170 and related instructions are additionally described elsewhere herein.

2.6. Seed Recommendation Subsystem

In an embodiment, the agricultural intelligence computer system 130, among other components, includes the seed recommendation subsystem 180. The seed recommendation subsystem 180 is configured to generate a set of target seeds specifically selected for optimal performance on target fields with minimized or reduced risk. The set of target seeds includes a subset of one or more seeds that have estimated yield forecasts above a specific yield threshold and have an associated risk value that is below a specific risk target.

In an embodiment, identifying a set of target seeds that will optimally perform on target fields is based on an input set of seeds that have been identified as having a specific probability of producing a successful yield on the target fields. The agricultural intelligence computer system 130 may be configured to receive a set of seeds as part of a target success yield group generated by the seed classification subsystem 170. The target success yield group may also include agricultural data specifying the probability of success for each seed and other agricultural data such as yield value, relative maturity, and environmental observations from previously observed harvests. In an embodiment, the agricultural intelligence computer system 130 also receives geo-location and agricultural data for a set of target fields. The "target fields" are fields where the grower is considering or intends to plant target seeds.

The seed filtering instructions 182 provide instructions to filter and identify a subset of seeds that have a probability of success value that is above a specified success yield threshold. The risk generation instructions 184 provide instructions to generate a dataset of risk values associated with each of the seeds. The risk values describe the amount of risk associated with each seed with respect to the estimated yield value for each seed. The optimization classification instructions 186 provide instructions to generate a dataset of target seeds that have average yield values above a target threshold for a range of risk values from the dataset of risk values.

In an embodiment, the agricultural intelligence computer system 130 is configured to present, via the presentation layer 134, the set of target seeds and including their average yield values.

Seed recommendation subsystem 180 and related instructions are additionally described elsewhere herein.

2.7. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the disclosure may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infrared data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infrared signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. Functional Overview—Generate and Display Target Success Yield Group of Seeds

FIG. 7 depicts a detailed example of generating a target success yield group of seeds identified for optimal yield performance on target fields based on agricultural data records of the seeds and geo-location data associated with the target fields.

3.1. Data Input

At step 705, the agricultural intelligence computer system 130 receives agricultural data records from one or more fields for multiple different seeds. In an embodiment, the agricultural data records may include crop seed data for one or more seeds. Crop seed data can include historical agricultural data related to the planting, growing, and harvesting of specific seeds on one or more fields. Examples of crop seed data may include, but are not limited to, historical yield values, harvest time information, and relative maturity of a seed, and any other observation data about the plant life cycle. For example, the agricultural data records may include seed data for two hundred (or more) different types of available soy varieties. The crop seed data associated with each of the soy varieties would include historical yield values associated with observed harvests, harvest time information relative to planting, and observed relative maturity for each of the soy varieties on each of the observed fields. For instance, a soy variety-001 may have agricultural data records that include historical yield data collected from twenty (or more) different fields over the past ten (or more) years.

In an embodiment, the agricultural data records may include field specific data related to the fields where the crop seed data was observed. For example, field specific data may include, but is not limited to, geo-location information, observed relative maturity based on field geo-location, historical weather index data, observed soil properties, observed soil moisture and water levels, and any other environmental observations that may be specific to the fields where historical crop seed data is collected. Field specific data may be used to further quantify and classify crop seed data as it relates to each of the seeds. For example, different fields in different geo-locations may be better suited for different seeds based on relative maturity of the seeds and the length of the growing season. Fields within specific regions and sub-regions may have an assigned relative maturity for the growing season that is based on the climate associated with the specific geo-location and the amount of growing degree days (GDDs) available during the growing season.

Figure 8:
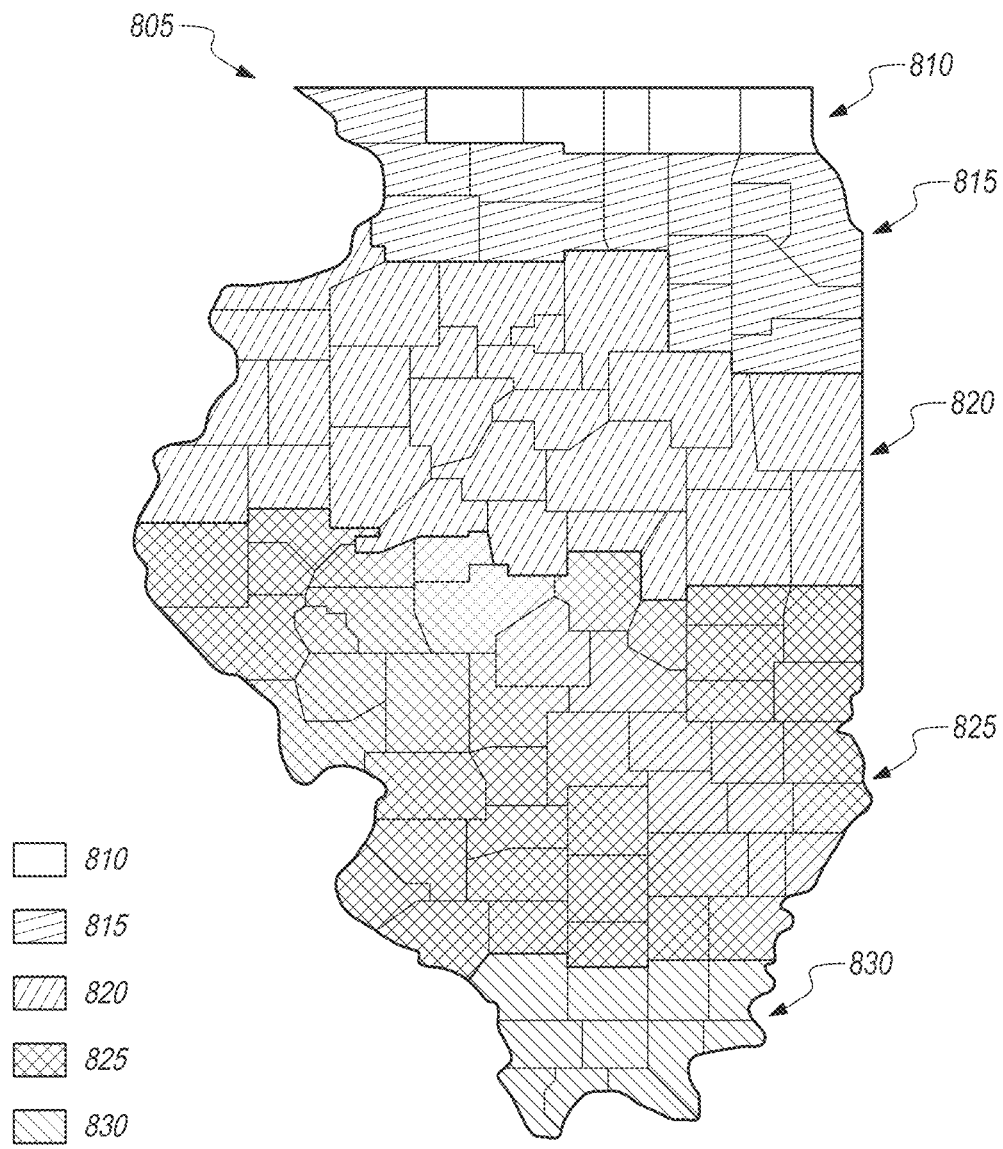
FIG. 8 depicts an example of different regions within a state that have different assigned relative maturity based on the growing season durations.

FIG. 8 depicts an example of different regions within a state that have different assigned relative maturity based on the growing season durations. State 805 is the state of Illinois and is divided into multiple different regions and sub-regions. Examples of sub-regions may include areas based on county, city, or town boundaries. Each of regions 810, 815, 820, 825, and 830 represent geo-location specific regions that have different growing season durations. For example, region 810 represents a region of fields that based upon their geo-locations and the associated climate have a shorter growing season because of cooler climates. As a result, region 810 may be classified as fields that are suited for seeds with a given relative maturity. Region 815 is located south of region 810 and as a result may have warmer overall climates. Fields in region 815 may be classified as fields suited for seeds with another relative maturity. Similarly, regions 820, 825, and 830 are located further south than regions 810 and 815, and as a result are classified with different relative maturity classifications, respectively. Relative maturity classifications for different regions may be used with historical yield data for seeds to assess how well seeds perform on fields based on rated relative maturities.

In an embodiment, specific field data within the agricultural data records may also include crop rotation data. Soil nutrient management for fields may depend on factors such as establishing diverse crop rotations and managing the amount of tillage of the soil. For example, some historical observations have shown that a "rotation effect" of rotating between different crops on a field may increase crop yield by 5 to 15% over planting the same crop year over year. As a result, crop rotation data within the agricultural data records may be used to help determine a more accurate yield estimation.

In an embodiment, specific field data may include tillage data and management practices used during the crop season. Tillage data and management practices refer to the manner and schedule of tillage performed on a particular field. Soil quality and the amount of useful nutrients in the soil varies based upon the amount of topsoil. Soil erosion refers to the removal of topsoil, which is the richest layer of soil in both organic matter and nutrient value. One such practice that causes soil erosion is tillage. Tillage breaks down soil aggregates and increases soil aeration, which may accelerate organic matter decomposition. Therefore, tracking tillage management practices may account for understanding the amount of soil erosion that occurs which may affect the overall yield of planted crop.

In an embodiment, the agricultural data records include historical crop seed data and field specific data from a set of test fields used to determine seed properties by manufacturers. For example, Monsanto Corporation produces several commercial hybrid seeds (e.g., corn hybrids) and seed varieties (e.g., soybean varieties) and tests their crop growth on multiple test fields. Monsanto Corp.'s test fields may serve as an example of a set of test fields where agricultural data records are collected and received by the agricultural intelligence computer system 130. In another embodiment, the agricultural data records may include historical crop seed data and field specific data from sets of fields owned and operated by individual growers. These sets of fields where agricultural data records are collected may also be the same fields designated as target fields for planting newly selected crops. In yet other embodiments, sets of fields owned and operated by a grower may provide agricultural data records used by other growers when determining the target success yield group of seeds.

Referring back to FIG. 7, at step 710, the agricultural intelligence computer system 130 receives geo-location information for one or more target fields. Target fields represent the fields where the grower is considering planting or planning to plant the set of seeds selected from the target success yield group. In an embodiment, the geo-location information for the one or more target fields may be used in conjunction with the agricultural data records of specific fields to determine which seeds, based on relative maturity and climate are best suited for the target fields.

3.2. Agricultural Data Processing

At step 715, the seed normalization instructions 172 provide instruction to generate a dataset of seed properties that describe representative yield values and environmental classifications for each seed received as part of the agricultural data records. In an embodiment, the agricultural data records associated with seeds are used to calculate a representative yield value and an environmental classification for each of the seeds. The representative yield value is an expected yield value for a specific seed if planted in a field based on the historical yield values and other agricultural data observed from past harvests.

In an embodiment, the normalized yield value may be calculated by normalizing multiple different yield observations from different fields across different observed growth years. For example, fields where a specific seed was first planted may be used to calculate an average first-year growth cycle yield for a specific seed. The average first-year growth cycle yield for the specific seed may include combining observed yield values from different fields over different years. For instance, the specific seed may have been planted on fields tested during the product stage of Monsanto's commercial product cycle (PS3, PS4, MD1, and MD2) over a time span of 2011 through 2017. However, the first cycle of the specific seed may have been planted on each of the fields on different years. The following table illustrates one such example:

|         | 2011 | 2012 | 2013 | 2014 | 2015 | 2016 | 2017 |
|---------|------|------|------|------|------|------|------|
| Cycle 1 | PS3  | PS4  | MD1  | MD2  |      |      |      |
| Cycle 2 |      | PS3  | PS4  | MD1  | MD2  |      |      |
| Cycle 3 |      |      | PS3  | PS4  | MD1  | MD2  |      |
| Cycle 4 |      |      |      | PS3  | PS4  | MD1  | MD2  |

The columns of the table represent harvest years and the rows of the table represent Monsanto commercial product development cycles, where cycle 1 represents the 4 years of the seeds planted on various fields and cycle 2 represents the second cycle of 4 years for another set of seeds planted on the same field environments and so on.

In an embodiment, calculating normalized yield values may be based on similar cycles for the seed planted at the multiple fields. For instance, the normalized yield value for cycle 1 may be calculated as an average of the yield values observed on fields PS3 (2011), PS4 (2012), MD1 (2013), and MD2 (2014). By doing so, yield values may be averaged based upon the common feature of how many growth cycles have occurred on the particular fields. In other embodiments, calculating normalized yield values may be based on other agricultural properties from the agricultural data records such as the same year or same region/field.

In an embodiment, the environmental classification for each of the seeds may be calculated using a relative maturity field property associated with agricultural data records of the seeds. For example, the specific seed may have been planted across several fields within region 820. Each of the fields within region 820 are classified as having an observed growth season that aligns with the specific relative maturity. Therefore, based on the fields associated with the specific seed, the environmental classification for the specific seed may be assigned a relative maturity that equals that of the region 820. In other embodiments, if the fields associated with historical observations of the specific seed contain fields classified within multiple regions then the environmental classification may be calculated as an average of the different assigned relative maturity values.

In an embodiment, the dataset of seed properties contains normalized yield values for each seed and an environmental classification that describes the relative maturity value associated with the normalized yield value. In other embodiments, the dataset of seed properties may also include properties related to the seed growth cycle and field properties such as crop rotations, tillage, weather observations, soil composition, and any other agricultural observations.

Referring back to FIG. 7, at step 720 the probability of success generation instructions 174 provide instruction to generate a dataset of success probability scores for each of the seeds which, describe a probability of a successful yield as a probabilistic value of achieving a successful yield relative to average yields of other seeds with the same relative maturity. In an embodiment, the success probability scores for the seeds are based upon the dataset of seed properties with respect to the geo-locations associated with the target fields. For example, relative maturity values associated with the geo-locations of the target fields are used in part to determine the set of seeds to evaluate against in order to calculate a success probability score for a particular seed. For instance, soy variety-002 may be a seed with a normalized yield value calculated as 7.5 bushels per acre and an assigned relative maturity. Soy variety-002 is then compared against other seeds that have similar relative maturity in order to determine whether soy variety-002 is a good candidate for planting based upon the normalized yield value of soy variety-002 and the other seeds.

Machine learning techniques are implemented to determine probability of success scores for the seeds at the geo-locations associated with the target fields. In an embodiment, the normalized yield values and assigned relative maturity values are used as predictor variables for machine learning models. In other embodiments, additional properties such as, crop rotations, tillage, weather observations, soil composition, may also be used as additional predictor variables for the machine learning models. The target variable of the machine learning models is a probabilistic value ranging from 0 to 1, where 0 equals a 0% probability of a successful yield and 1 equals a 100% probability of a successful yield. In other embodiments, the target variable may be a probabilistic value that may be scaled from 0 to 10, 1 to 10, or any other scale of measurement. A successful yield is described as the likelihood that the yield of a specific seed is a certain value above the mean yield for similarly classified seeds. For example, a successful yield may be defined as a yield that is 5 bushels per acre above the mean yield of seeds that have the same assigned relative maturity value.

Figure 9:
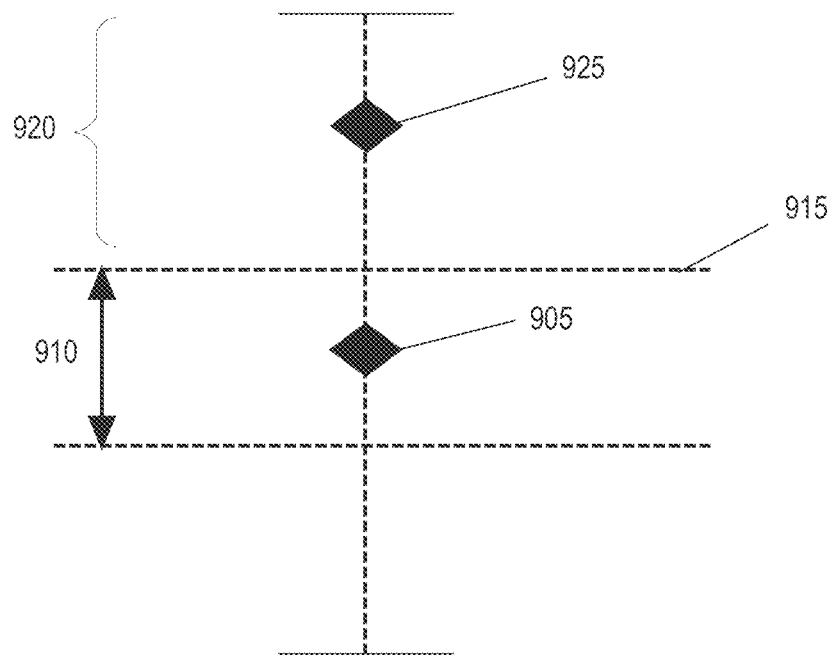
FIG. 9 depicts a graph describing the range of normalized yield values for seeds within a classified relative maturity.

FIG. 9 depicts a sample graph describing the range of normalized yield values for seeds within a classified relative maturity. Mean value 905 represents the calculated mean yield value for seeds that have the same relative maturity group. In an embodiment, determining which seeds have a significant normalized yield above the mean value 905 may be calculated by implementing a least significant difference calculation. The least significant difference is a value at a particular level of statistical probability. If the value is exceeded by the difference between two means, then the two means are said to be distinct. For example, if the difference between yield values of a seed and the calculated mean yield exceeds the least significant difference value, then the yield for the seed is seen as distinct. In other embodiments, determining significant differences between yield values and the mean value 905 may be determined using any other statistical algorithm.

Range 910 represents a range of yield values that are considered within the least significant difference value, and therefore are not significantly distinct. Threshold 915 represents the upper limit of the range 910. Normalized yield values above threshold 915 are then considered to be significantly distinct from the mean value 905. In an embodiment, range 910 and threshold 915 may be configured to represent a threshold for determining which seed yields are considered to be significantly higher than the mean value 905 and therefore a successful yield value. For example, threshold 915 may be configured to equal a value that is 5 bushels per acre above the mean value 905. In an embodiment, threshold 915 may be configured as a yield value that is dependent on the mean value 905, range 910, and the overall range of yield values for the specific seeds that have the same relative maturity.

Range 920 represents a range of yield values for seeds that are considered successful yields. Seed 925 represents a specific hybrid seed or seed variety within the range 920 that has a normalized yield value above the threshold 915. In an embodiment, machine learning models may be configured to use the range 910 and threshold 915 when calculating probability of success scores between 0 and 1. Different machine learning models may include, but are not limited to, logistic regression, random forest, vector machine modelling, and gradient boost modelling.

In an embodiment, logistic regression may be implemented as the machine learning technique to determine probability of success scores for each of the seeds for the target fields. For logistic regression, the input values for each seed are the normalized yield value and the environmental classification, which is specified as relative maturity. The functional form of the logistic regression is:

$$P(y=1 \mid x_1 = \underline{yld_i}, x_2 = \underline{RM_j}) = \frac{e^{a+b*x_1+c*x_2}}{1+e^{a+b*x_1+c*x_2}},$$

where $P(y=1 \mid x_1 = \underline{yld_i}, x_2 = \underline{RM_j})$ is the probability of success (y=1) for product i with normalized yield value and in target field j with a given relative maturity; constants a, b and c are the regression coefficients estimated through historical data. The output of the logistic regression is a set of probability scores between 0 and 1 for each seed specifying success at the target field based upon the relative maturity assigned to the geo-location associated with the target fields.

In another embodiment, a random forest algorithm may be implemented as the machine learning technique to determine probability of success scores for each of the seeds for the target fields. Random forest algorithm is an ensemble machine learning method that operates by constructing multiple decision trees during a training period and then outputs the class that is the mean regression of the individual trees. The input values for each seed are the normalized yield value and the environmental classification as relative maturity. The output is a set of probability scores for each seed between 0 and 1.

In another embodiment, support vector machine (SVM) modelling may be implemented as the machine learning technique to determine probability of success scores for each of the seeds for the target fields. Support vector machine modelling is a supervised learning model used to classify whether input using classification and regression analysis. Input values for the support vector machine model are the normalized yield values and the environmental classification relative maturity values for each seed. The output is a set of probability scores for each seed between 0 and 1. In yet another embodiment, gradient boost (GBM) modelling may be implemented as the machine learning technique, where the input values are the normalized yield values and the environmental classification relative maturity values for each seed. Gradient boost is a technique for regression and classification problems, which produces a prediction model in the form of an ensemble of weak prediction models, such as decision trees.

Referring to FIG. 7, at step 725 the yield classification instructions 176 generate a target success yield group made up of a subset of the seeds that have been identified as having a high probability to produce a yield that is significantly higher than the average yield for other seeds within the same relative maturity classification for the target fields. In an embodiment, the target success yield group contains seeds that have probability of success values that are above a specific success probability threshold. The success probability threshold may be configured probability value that is associated with yields that are significantly higher than the mean yield of other seeds. For example, if at step 720 the yield threshold for successful yields is equal to five bushels per acre above the mean value, then the success probability threshold may be associated with a probability of success value equal to that of the yield threshold. For instance, if the yield threshold equals five bushels per acre above the mean yield and has a probability of success value as 0.80 then the success probability threshold may be assigned 0.80. In this example, the target success yield group would contain seeds that have probability of success values equal to or greater than 0.80.

In other embodiments, the success probability threshold may be configured to be higher or lower depending on whether the grower desires a smaller or larger target success yield group respectively.

3.3. Present Target Success Yield Group

In an embodiment, the target success yield group contains seeds that have an assigned relative maturity value that equals the relative maturity associated with the target fields. At step 730, the presentation layer 134 of the agricultural intelligence computer system 130 is configured to display or cause display, on a display device on the field manager computing device 104, of the target success yield group and normalized yield values for each seed within the target success yield group. In another embodiment, the presentation layer 134 may communicate the display of the target success yield group to any other display devices that may be communicatively coupled to the agricultural intelligence computer system 130, such as remote computer devices, display devices within a cab, or any other connected mobile devices. In yet another embodiment, the presentation layer 134 may communicate the target success yield group to other systems and subsystems with the agricultural intelligence computer system 130 for further processing and presentation.

In an embodiment, the presentation layer 134 may display additional seed property data and other agricultural data that may be relevant to the grower. The presentation layer 134 may also sort the seed in the target success yield group based on the probability of success values. For example, the display of seeds may be sorted in descending order of probability of success values such that the grower is able to view the most successful seeds for his target fields first.

In some embodiments, after receiving the information displayed, a grower may act on the information and plant the suggested seeds. In some embodiments, the growers may operate as part of the organization that is determining the target success yield group, and/or may be separate. For example, the growers may be clients of the organization determining the target success yield group and may plant seed based on the target success yield group.

4. Functional Overview—Generating and Displaying Target Seeds for Planting

Figure 10:
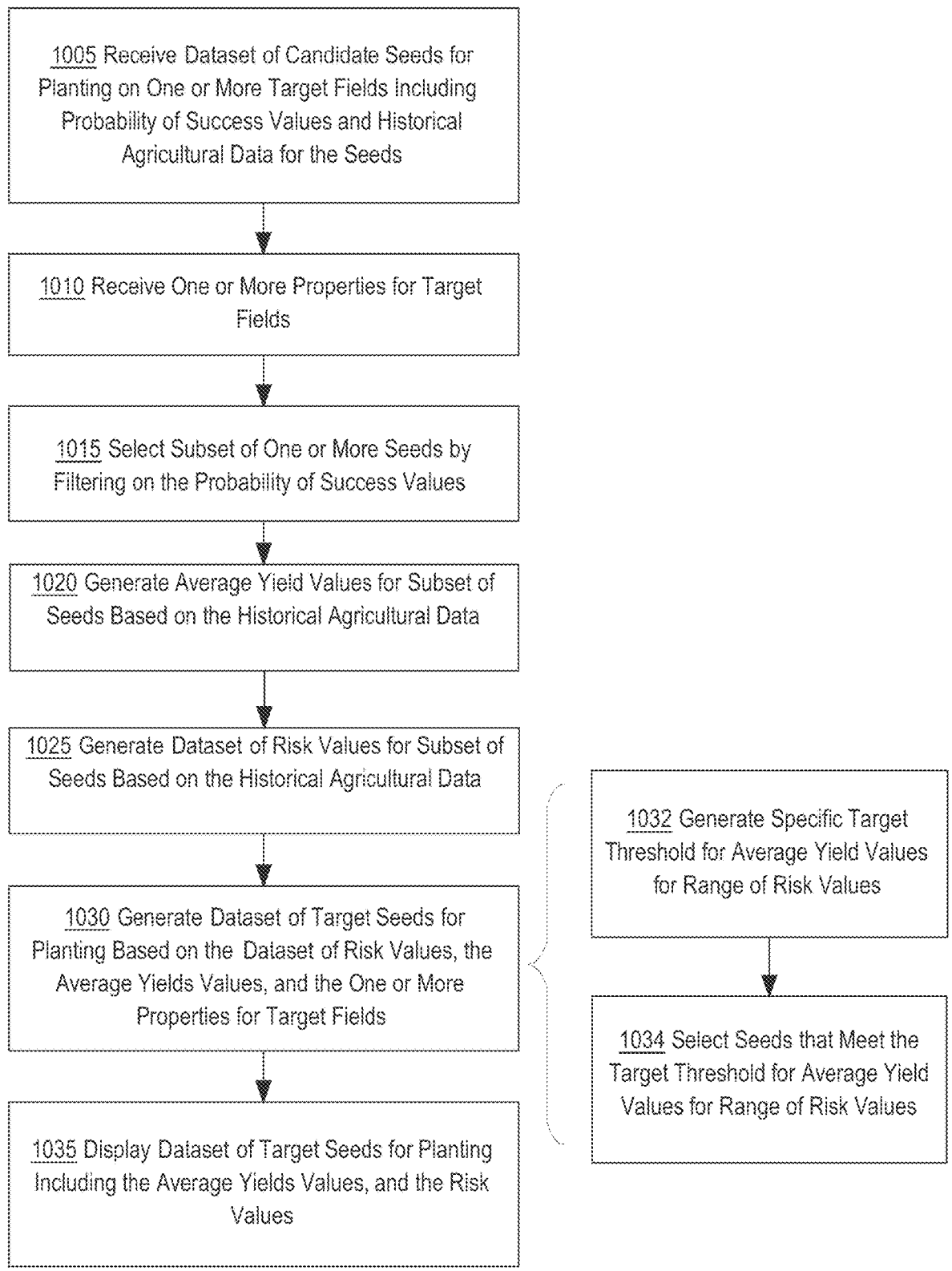
FIG. 10 depicts an example flowchart for generating a set of target seeds identified for optimal yield performance and managed risk on target fields based on agricultural data records of the seeds and geo-location data associated with the target fields.

FIG. 10 depicts a detailed example of generating a set of target seeds identified for optimal yield performance and managed risk on target fields based on agricultural data records of the seeds and geo-location data associated with the target fields.

4.1. Data Input

At step 1005, the agricultural intelligence computer system 130 receives a dataset of candidate seeds including one or more seeds suited for planting on target fields, probability of success values associated with each seed, and historical agricultural data associated with each seed. In an embodiment, the dataset of candidate seeds may include a set of one or more seeds identified by the seed classification subsystem 170 as having a high probability to produce successful yield values on the target fields and historical agricultural data associated with each seed in the set of candidate seeds. The target success yield group generated at step 725 in FIG. 7 may represent the dataset of candidate seeds.

In an embodiment, the historical agricultural data may include agricultural data related to the planting, growing, and harvesting of specific seeds on one or more fields. Examples of agricultural data may include, but are not limited to, historical yield values, harvest time information, and relative maturity of a seed, and any other observation data about the plant lifecycle. For example, if the dataset of candidate seeds is the target success yield group from the seed classification subsystem 170, then the agricultural data may include an average yield value and a relative maturity assigned to each seed.

At step 1010, the agricultural intelligence computer system 130 receives data about the target fields where the grower is planning to plant the set of target hybrid seeds and/or seed varieties. In an embodiment, the data about the target fields is property information that includes, but is not limited to, geo-location information for the target fields and dimension and size information for each of the target fields. In an embodiment, the geo-location information for the target fields may be used in conjunction with the historical agricultural data to determine optimal set of target seeds and amount of each of the target seeds to plant on each of the target fields based on relative maturity and climate of the target fields.

4.2. Seed Selection

At step 1015, the seed filtering instructions 182 provide instruction to select a subset of one or more seeds from the candidate set of seeds that have a probability of success value greater than or equal to a target probability filtering threshold. In an embodiment, the target probability filtering threshold is a configured threshold of the probability of success value associated with each of the seeds in the candidate set of seeds. The target probability filtering threshold may be used to further narrow the selection pool of seeds based upon only selecting the seeds that have a certain probability of success. In an embodiment, if the candidate set of seeds represents the target success yield group generated at step 725, then it is likely that the set of seeds have already been filtered to only include seeds with a high probability of success value. In one example, the target probability filtering threshold may have the same threshold value as the successful yield threshold used to generate the target success yield group. If that is the case, then the subset of one or more seeds may include the entire set of seeds. In another example, the grower may desire a more narrowed list of seeds, which may be achieved by configuring a higher probability of success value for the target probability filtering threshold to filter out the seeds that have lower than desired probability of success values.

At step 1020, the seed normalization instructions 172 provide instruction to generate a representative yield value for each seed in the subset of one or more seeds based on yield values from the historical agricultural data for each of the seeds. In an embodiment, representative yield value is an expected yield value for a specific seed if planted in a field based on the historical yield values and other agricultural data observed from past harvests. In an embodiment, the representative yield value is a calculated average of yields from multiple different observed growth seasons on multiple fields. For example, the representative yield value may be calculated as an average of different observed growth cycle years, where an average first-year growth cycle yield for the specific seed may incorporate combining observed yield values from different fields over different years. After calculating average growth cycle yields for different growth cycle years, each of the averages may be combined to generate a representative average yield for each specific seed. In another embodiment, the representative yield value may be the normalized yield value calculated at step 715.

4.3. Generate Risk Values for Seeds

At step 1025, the risk generation instructions 184 provide instruction to generate a dataset of risk values for each hybrid seed or seed variety in the subset of one or more seeds based upon historical agricultural data associated with each of the seeds. Risk values describe the amount of risk, in terms of yield variability, for each seed based upon the representative yield value. For example, if for soy variety-002 the representative yield is fifteen bushels per acre however, the variability for soy variety-002 is high such that the yield may range from five bushels per acre to twenty-five bushels per acre, then it is likely that the representative yield for soy variety-002 is not a good representation of actual yield because the yield may vary between five and twenty-five bushels per acre. High risk values are associated with high variability on yield return, whereas low risk values are associated with low variability on yield return and yield outcomes that are more closely aligned to the representative yield.

In an embodiment, risk values for seeds are based on the variability between year-to-year yield returns for a specific seed over two or more years. For example, calculating a risk value for soy variety-002 includes calculating the variability of yield values from multiple years of yield output from the historical agricultural data. The variance in yield output from 2015 and 2016 for soy variety-002 may be used to determine a risk value that may be associated with the representative yield value for soy variety-002. Determining the variance of yield output is not limited to using yield output from two previous years, variance may be calculated with yield output data from multiple years. In an embodiment, the calculated risk values may be represented in terms of a standard deviation of bushel per acre, where standard deviation is calculated as the square root of the calculated variance of risk.

In an embodiment, risk values for seeds may be based on the variability of yield output from field-to-field observations for a specific year. For example, calculating a risk value associated with field variability may include determining the variability of yields from each field observed for a specific seed for a specific year. If for a specific seed the observed yield output across multiple fields ranges from five to fifty bushels per acre, then the specific seed may have high field variability. As a result, the specific seed may be assigned a high-risk factor based on field variability because expected output on any given field may vary between five to fifty bushels per acre instead of being closer to the representative yield value.

In another embodiment, risk values for seeds may be based upon variability between year-to-year yield returns and variability between field-to-field observations. Both the year-to-year risk values and the field-to-field risk values may be combined to represent a risk value that incorporates variability of yield output across multiple observed fields and multiple observed seasons. In yet other embodiments, risk values may incorporate other observed crop seed data associated with historical crop growth and yield.

4.4. Generate Dataset of Target Seeds

At step 1030, the optimization classification instructions 186 provide instruction to generate a dataset of target seeds for planting on the target fields based on the dataset of risk values, the representative yield values for the seeds, and the one or more properties for the target fields. In an embodiment, the target seeds in the dataset of target seeds are selected based upon their representative yield values and the associated risk values from the dataset of risk values.

Determining which combination of seeds to include in the dataset of target seeds involves determining a relationship between the representative yield for a specific seed and the risk value associated with the specific seed. Choosing seeds that have high representative yields may not result in an optimal set of seeds if the high yield seeds also carry a high level of risk. Conversely, choosing seeds that have low risk values may not have a high enough yield return on investment.

Figure 11:
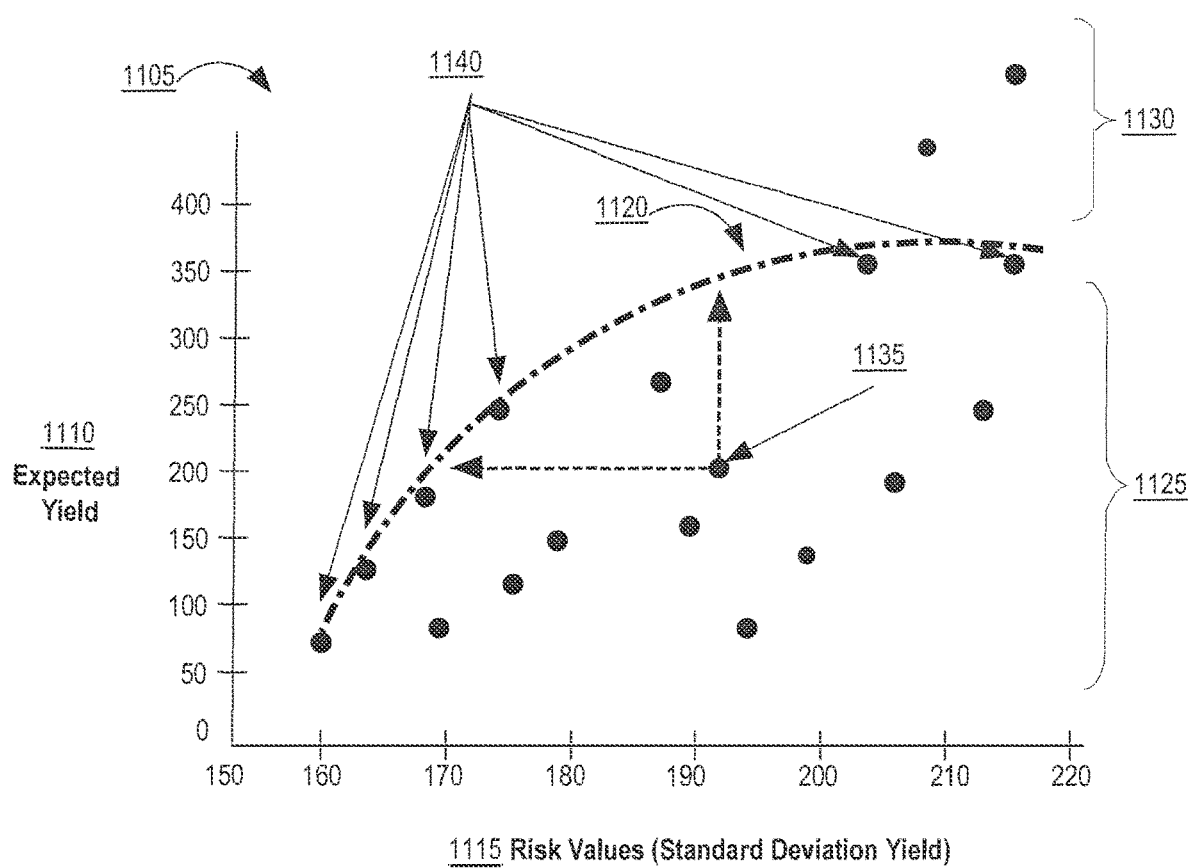
FIG. 11 depicts an example graph of yield values versus risk values for one or more seeds.

In an embodiment, the seeds from the subset of one or more seeds may be graphed based on their respective representative yield values versus their associated risk values. FIG. 11 depicts an example graph 1105 of yield versus risk for the subset of one or more seeds. The y-axis 1110 represents the representative yield, as expected yield, for the seeds and the x-axis 1115 represents the risk values for the seeds expressed as standard deviation. By representing risk values as standard deviation, the unit of the risk values may be the same as the units for representative yield, which is bushels per acre. Dots on graph 1105, represented by group 1125 and group 1130 represent each of the seeds from the subset of one or more seeds. For example, graph 1105 shows that seed 1135 has a representative yield value two hundred bushels per acre and a risk value having a standard deviation of one hundred ninety-one bushels per acre. In other embodiments, graph 1105 may be generated using different units such as profit per acre measured in dollars or any other derived unit of measurement.

In an embodiment, determining which seeds belong in the dataset of target seeds involves determining an expected yield return for a specified amount of risk. To generate set of target seeds that will likely be resilient to various environmental and other factors, it is preferable to generate a diverse set of seeds that contains seeds with both lower and higher risk values as well as moderate to high yield output. Referring to FIG. 10, step 1032 represents generating a target threshold of representative yield values for a range of risk values. In an embodiment, the optimization classification instructions 186 provide instruction to calculate an optimal frontier curve that represents a threshold of optimal yield output with a manageable amount of risk tolerance over the range of risk values. A frontier curve is a fitted curve that represents the optimal output with respect to the graphed input values considering optimal efficiency. For example, graph 1105 contains seeds based on representative yield versus risk value, where it may be inferred that a specific seed that has a higher yield is likely to also have higher risk. Conversely, seeds that have lower risk values are likely to have lower representative yield values. Frontier curve 1120 represents an optimal curve that tracks the optimal amount of yield based on a range of risk values.

At step 1034, the optimization classification instructions 186 provide instruction to select seeds that make up the set of target seeds by selecting the seeds that have a representative yield and risk value that meets the threshold defined by the frontier curve 1120. Seeds that fall on or near the frontier curve 1120 provide the optimal level of yield at the desired level of risk. Target seeds 1140 represent the optimal set of seeds for the dataset of target seeds. Seeds that fall under the frontier curve 1120 have sub-optimal yield output for the level of risk or have higher than desired risk for the level of yield output produced. For example, seed 1135 is under the frontier curve 1120 and may be interpreted as having lower than optimal yield for its amount of risk, as shown by the placement of seed 1135 being vertically below the frontier curve 1120. Also, seed 1135 may be interpreted as having higher than expected risk for its yield output, as shown by the placement of seed 1135 being horizontally to the right of the frontier curve 1120 for that amount of representative yield. Seeds 1135 that are not on or near the frontier curve 1120 have sub-optimal representative yield for their associated risk values and are therefore not included in the set of target seeds. Additionally, seeds 1135 represent seeds that have a higher than desired risk value and are therefore not included in the set of target seeds.

In an embodiment, the optimization classification instructions 186 provide instruction to generate allocation instructions for each target seed in the set of target seeds. Allocation instructions describe an allocation quantity of seeds for each target seed in the set of target seeds that provide an optimal allocation strategy to a grower based upon the amount and location of the target fields. For example, allocation instructions for a set of target seeds that includes seeds (CN-001, CN-002, SOY-005, CN-023) may include an allocation of 75% of CN-001, 10% of CN-002, 13% of SOY-005, and 2% of CN-023. Embodiments of the allocation instructions may include, but are not limited to, number of bags of seeds, a percentage of the total seeds to be planted across the target fields, or an allotment number of acres for each target seed to be planted. In an embodiment, determining allocation amounts may be calculated using a third-party optimization solver product, such as CPLEX Optimizer by IBM. The CPLEX Optimizer is a mathematical programming solver for linear programming, mixed integer programming, and quadratic programming. Optimization solvers, such as CPLEX Optimizer, are configured to evaluate the representative yield values and risk values associated with the target seeds and determine a set of allocation instructions for allocating amounts of seeds for each of the target seeds in the set of target seeds. In an embodiment, the optimization solver may use the sum of the representative yield values of target seeds and a calculated sum of risk values of the target seeds to calculate a configured total risk threshold that may be used to determine the upper limits of allowed risk and yield output for the set of target seeds.

In another embodiment, the optimization solver may also input target field data describing size, shape, and geo-location of each of the target fields, in order to determine allocation instructions that include placement instructions for each of the allotments of target seeds. For example, if a particular target field is shaped or sized in a particular way, the optimization solver may determine that allotment of one target seed is preferable on the particular field as opposed to planting multiple target seeds on the particular field. The optimization solver is not limited to the CPLEX Optimizer, other embodiments may implement other optimization solvers or other optimization algorithms to determine sets of allocation instructions for the set of target seeds.

4.5. Seed Portfolio Analysis

Step 1030 described determining and generating the set of target seeds for a grower based on the target fields using the frontier curve to determine the optimal yield output for the desired level of risks. In an embodiment, the optimization classification instructions 186 provide instruction to configure the frontier curve to determine overall optimal performance for a grower's seed portfolio relative to other growers within the same region or sub-region. For example, representative yield output and overall risk values may be calculated for each grower within a specific region. For example, using historical agricultural data for multiple growers, the representative yield values and associated risk values for seeds planted by each grower may be aggregated to generate an aggregated yield output value and aggregated risk value associated with each grower. Then the aggregated values for each grower may be graphed on a seed portfolio graph, similar to graph 1105, where the individual dots on the graph may represent a grower's aggregated seed yield output and aggregated risk. In an embodiment, the frontier curve may be generated to determine an optimal aggregated yield output and aggregated risk value for the growers in the specific region. Growers that are on or near the frontier curve may represent growers whose seed portfolio produces the optimal amount of yield with a managed amount of risk. Growers that are below the frontier curve represent growers that are not maximizing their output based on their risk.

In an embodiment, the optimization classification instructions 186 provide instruction to generate an alert message for a particular grower if the aggregated yield output and aggregated risk for the grower's seed portfolio does not meet the optimal threshold for the seed portfolio as described by the frontier curve on a seed portfolio graph. The presentation layer 134 may be configured to present and send the alert message to the field manager computing device 104 for the grower. The grower may then have the option of requesting a set of target seeds that may provide optimal yield output for future growing seasons.

4.6. Present Set of Target Seeds

In an embodiment, the dataset of target seeds may contain the representative yield values and risk values, from the dataset of risk values, associated with each target seed in the dataset of target seeds for the target fields. Referring to FIG. 10, at step 1035 the presentation layer 134 of the agricultural intelligence computer system 130 is configured to communicate a display, on a display device on the field manager computing device 104, of the dataset of target seeds including the representative yield values and associated risk values for each target seed. In another embodiment, the presentation layer 134 may communicate the display of the dataset of target seeds to any other display devices that may be communicatively coupled to the agricultural intelligence computer system 130, such as remote computer devices, display devices within a cab, or any other connected mobile devices. In yet another embodiment, the presentation layer 134 may communicate the dataset of target seeds to other systems and subsystems with the agricultural intelligence computer system 130 for further processing and presentation.

In an embodiment, the presentation layer 134 may display allocation instructions, including seed allotments and placement information, for each target seed. The presentation layer 134 may also sort the target seeds based on allotment quantity or may present the target seeds based on placement strategy on the target fields. For example, the display of target seeds and allocation instructions may be superimposed onto a map of the target fields so that the grower may visualize planting strategy for the upcoming season.

In some embodiments, growers can take in the information presented related to allocation instructions and plant seeds based on the allocation instructions. The growers may operate as part of the organization that is determining the allocation instructions, and/or may be separate. For example, the growers may be clients of the organization determining the allocation instructions and may plant seed based on the allocation instructions.

5. Functional Overview—Generate and Display Yield Improvement Recommendation by Field As noted above, embodiments disclosed herein are useful to identify seed products that will optimally perform on target fields based on input received by the agricultural intelligence computer system 130. Such input may comprise agricultural data and historical yield data for different seeds and environment data related to the field of a grower where the seed data was observed. In addition to grower data, the agricultural intelligence computer system 130 may also utilize seed and environment data observed during different breeding and development stages associated with seeds. This data is valuable and continues to grow over time as harvests are analyzed, environmental conditions change, unique field locations are added, and new and existing seeds are further developed and tested. Even so, seeds cannot be tested at every field location or under every potential combination of environmental conditions.

In embodiments, the data used in the disclosed machine learning models are enriched by using genetic data to generate agricultural data for seeds that have not been tested under particular environmental conditions. For instance, the disclosed techniques use genetics data by obtaining and using germplasm (base genetics+trait) and/or pedigree information, genetic cluster patterns, and/or genomic marker relationships to impute yield data in different environments. All such data is digitally stored, retrieved, and transformed using computer-implemented instructions.

Figure 12:
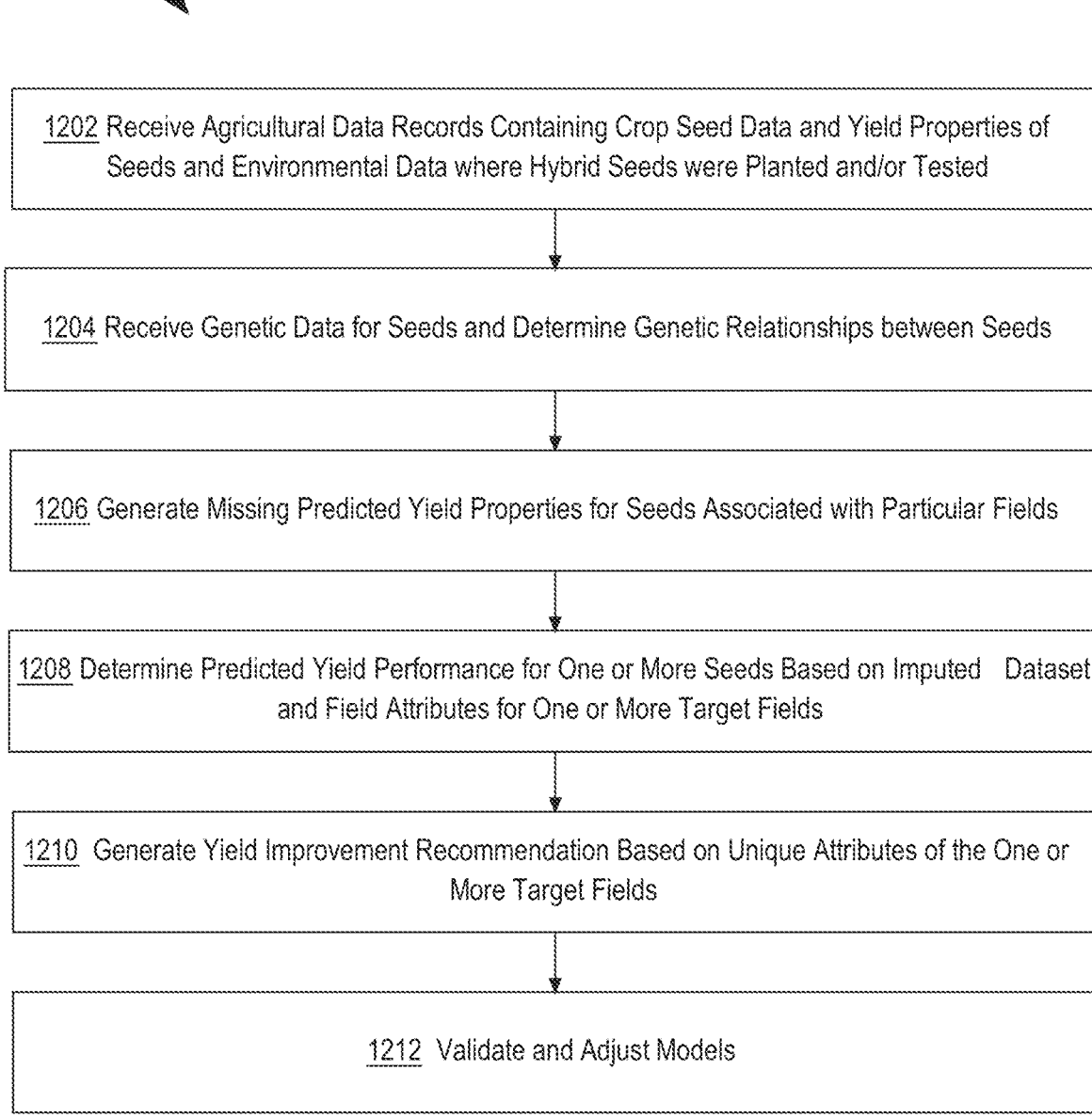
FIG. 12 illustrates an example flowchart for utilizing genetics to fill data gaps in historical agricultural data.

FIG. 12 illustrates an example flowchart that includes utilizing genetics to fill data gaps in historical agricultural data. The resulting agricultural data is thereby enhanced with predictive, imputed data, which can form a basis for improved seed placement calculation strategies in actual fields having particular environmental conditions. According to one example, the agricultural intelligence computer system 130 of FIG. 1 is programmed or configured to perform the functions of flowchart 1200 of FIG. 12. For instance, the seed classification subsystem 170 and/or the seed recommendation subsystem 180 may include genetic modeling instructions as described further herein.

5.1. Data Input

At block 1202, the agricultural intelligence computer system 130, for example, receives or otherwise accesses agricultural data records. In one example, computer system 130 receives the agricultural data records over a digital data communication network 109. The agricultural data records include, for instance, crop seed data and yield properties of seeds and environmental data where the seeds were planted and/or tested.

Figure 13:
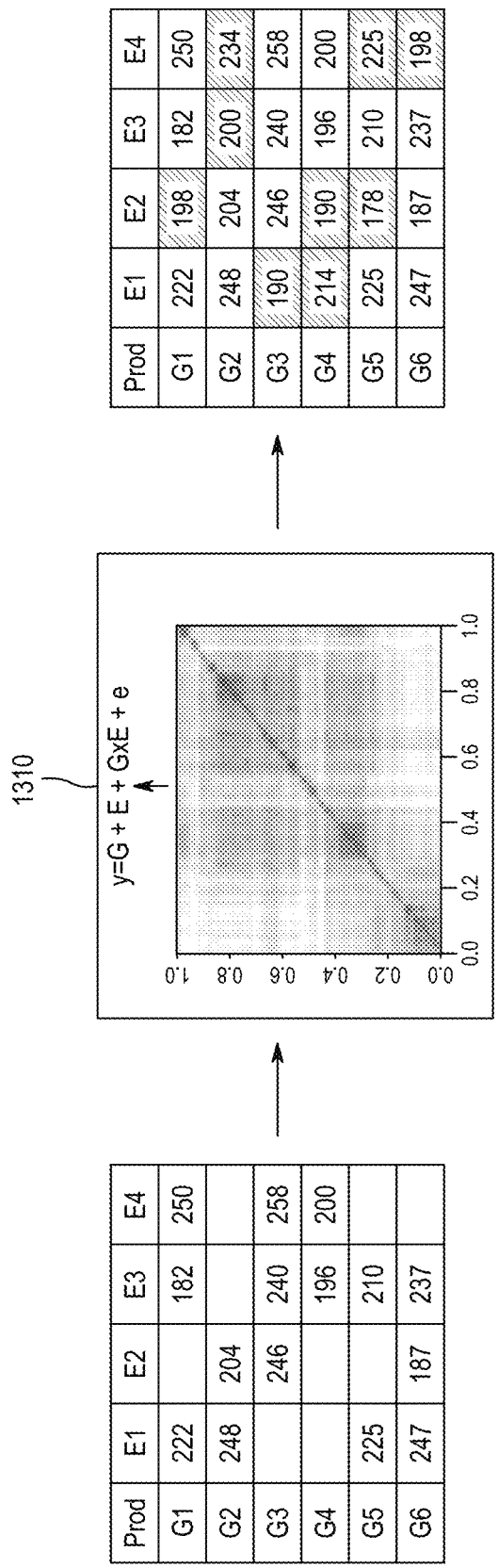
FIG. 13 illustrates an example of received agricultural data records and further processing to fill data gaps.

FIG. 13 illustrates an example of received agricultural data records and further processing to impute data values. In FIG. 13, the received agricultural data records include seed products G1, G2, G3, G4, G5, G6 and yield data is provided in bushels per acre (bu/ac), for example, associated with different fields or environments E1, E2, E3, E4. The yield data can be associated with a particular year or harvest and additional data records can be received for other years/harvests, and/or the yield data can be an average yield or other representation of multi-year data. Assume as an example that seed product G1 was planted in field E1 and was associated with an actual yield of 222 bu/ac. The received agricultural data records, however, lack selected yield data that should be associated with a given seed product in a given field. In FIG. 13, for instance, no yield data is associated with seed product G3 in field E1. Such data gaps can be caused by a given seed not having been planted in a given field or other reasons. As a practical matter, actual field or lab testing of each seed in each combination of unique environmental conditions is not possible.

Figure 14:
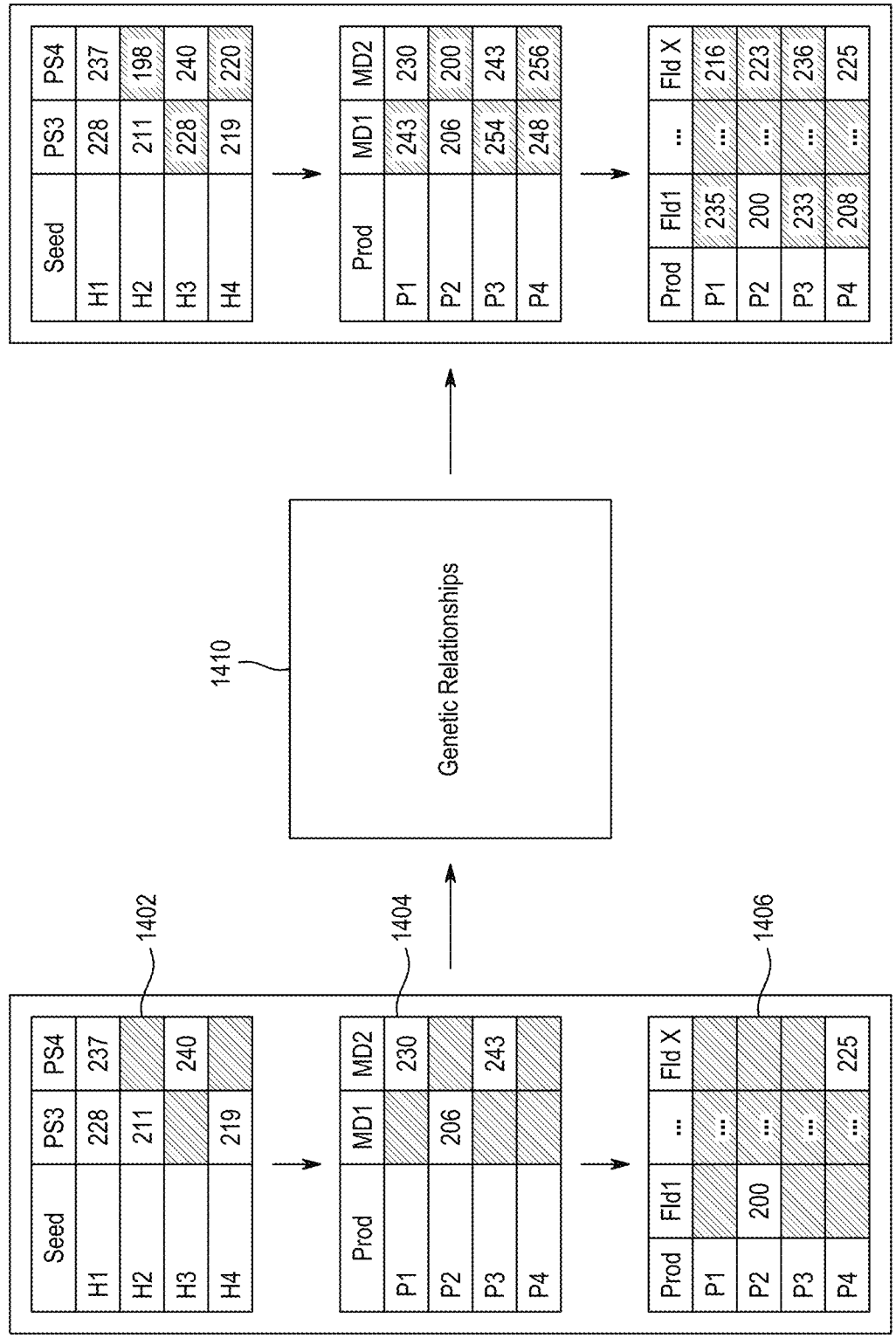
FIG. 14 illustrates another example of received agricultural data records and further processing to fill data gaps.

FIG. 14 illustrates another example of received agricultural data records and further processing to fill data gaps. In FIG. 14, the data records are provided for different product stages. For instance, data records 1402 are associated with an early product development or breeding stage, data records 1404 are associated with a subsequent product development or commercial testing stage, and data records 1406 are associated with a field-use stage. The first column in each data record identifies different seeds (e.g., corn hybrid) at the breeding stage H1, H2, H3, H4, and seed products at the commercial testing and field-use stages P1, P2, P3, P4. For purposes of this discussion, the seeds H1, H2, H3, H4 advanced from the breeding stage and were re-named or later-identified as corresponding seed products P1, P2, P3, P4, respectively, in the other stages.

The top row in data record 1402 identifies different testing cycles PS3, PS4, which may be defined by a given time period, such as one-year, and that are associated with unique environmental conditions. The top row in data record 1404 identifies different additional testing cycles MD1, MD2, which may be similarly defined by a given time period, such as one-year, and that are associated with perhaps other unique environmental conditions. The top row in data record 1406 identifies cycles associated with different fields or environments Fld1-FldX where the seed products were grown and harvested to provide yield data.

Similarly to the received agricultural data records in FIG. 13, the data records in FIG. 14 also have data gaps where no yield data is associated with a given seed product in a given field or testing environment. Even with the data gaps, however, the agricultural data records represented by FIG. 13 and FIG. 14 provide a wealth of information for perhaps a thousand or more seeds in tens of thousands of field locations and testing conditions, and over numerous product stages, testing cycles, and planting and harvesting cycles over many years. The present embodiment uses genetic relationships to further enhance and build upon this wealth of information. The received agricultural data records may be associated with a wide range of feature data related to the seeds, environmental and/or testing conditions, and yield properties. General categories of such feature data relate to the weather, soil conditions, environmental classifications, field management practices, pest risks, genetic features, and overall genomic-by-environment features (G×E features) that capture non-additive interactions between genetic and environmental features. Other categories of such feature data include genomic-by-management features (G×M) and genomic-by-environment-by-management features (G×E× M), which respectively capture non-additive interactions between genetic and management features, and interactions between genetic, environment, and management features. Various particular features within such categories are provided herein.

Referring back to FIG. 12, at block 1204, the computer system 130 receives or otherwise accesses genetic feature data related to the seeds. The genetic data may include genetic relationships between seeds. Although, in one example, the computer system 130 uses received raw genetic feature data to develop such genetic relationships between the seeds. In one example, the agricultural data records received or accessed at block 1202 is related to a first set of seeds, the genetic feature data received or accessed at block 1204 is related to a second set of seeds, and the second set of seeds includes the first set of seeds. In some embodiments, genetic feature data and/or the genetic relationships may be commercially obtained from the Crop Science division of Bayer AG, Leverkusen, Germany.

Figure 15:
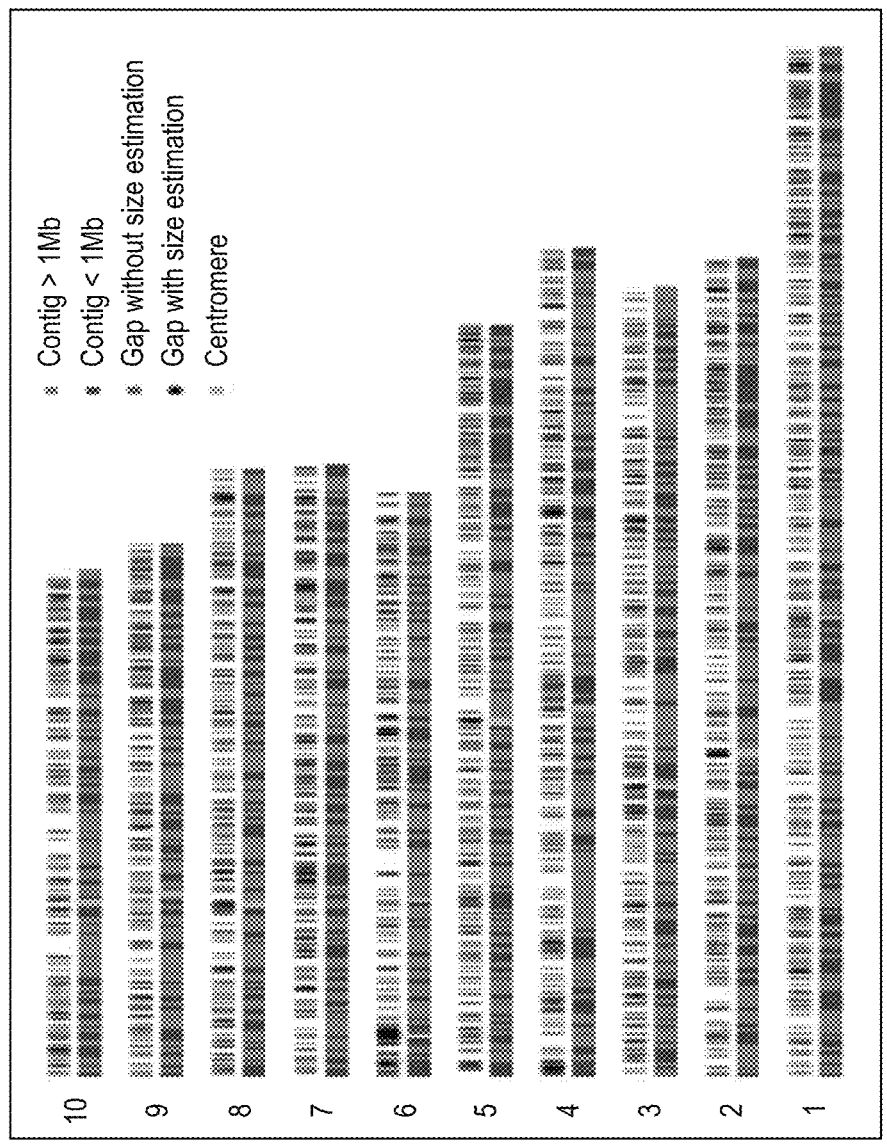
FIG. 15 illustrates an example of the genetic feature data including genomic marker data.

FIG. 15 illustrates an example of the genetic feature data including genomic marker data. Genomic marker data is generally a gene or DNA sequence that can be used to identify unique gene characteristics. In one example, the genomic marker data may incorporate whole-genome single nucleotide polymorphism (SNP) markers found in the seeds, as represented by genes 1-10 in FIG. 15.

Figure 16:
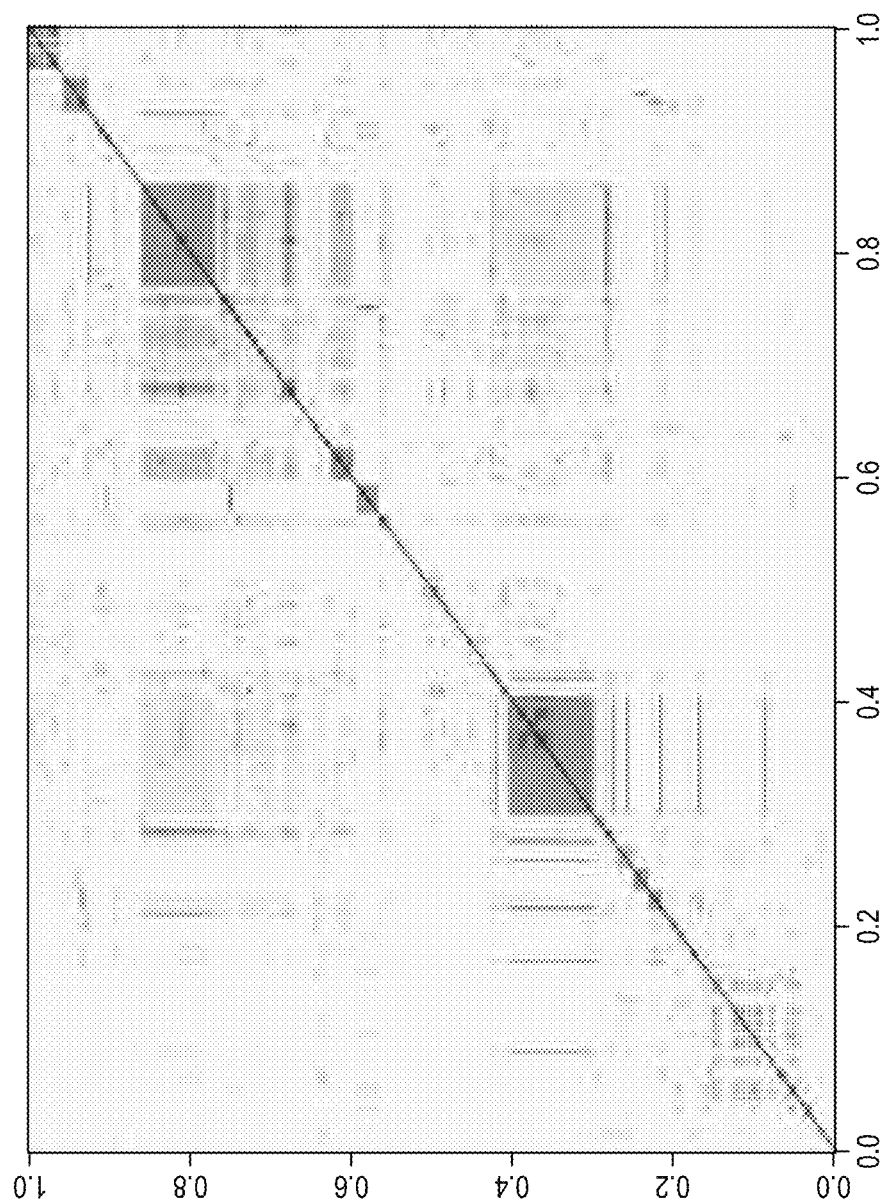
FIG. 16 illustrates an example pedigree-based kinship matrix that identifies pairwise relationships between seeds based on seed pedigree.

FIG. 16 illustrates an example pedigree-based kinship matrix that identifies pairwise relationships between seeds based on seed pedigree. The relationship is captured by a value between 0.0 and 1.0, wherein a value of 0.0 means that the two seeds are completely different and unrelated according to pedigree, and a value of 1.0 means that the two seeds have an identical pedigree.

Figure 17:
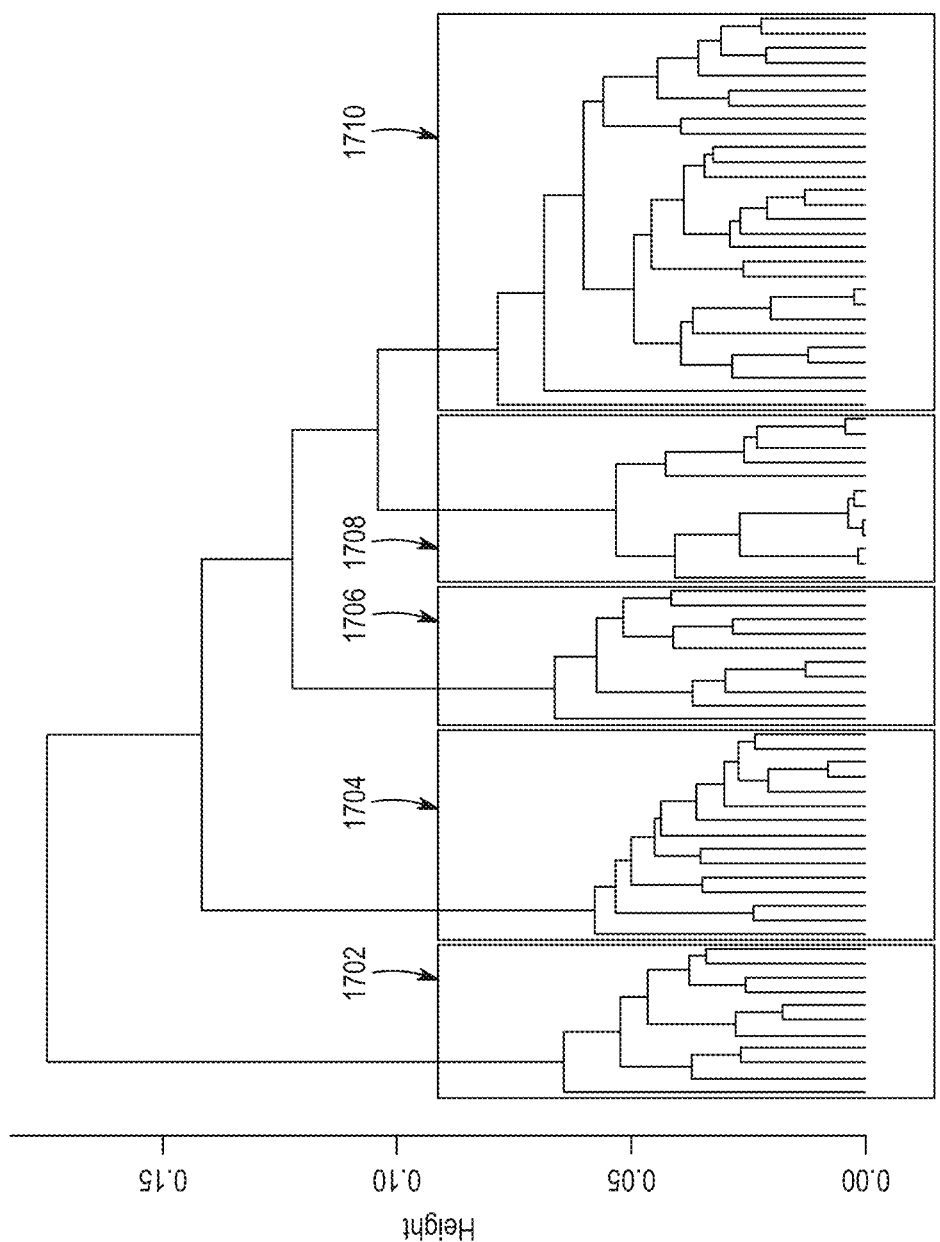
FIG. 17 illustrates an example that organizes seeds into genetic cluster relationships.

FIG. 17 illustrates an example that organizes seeds into genetic cluster relationships. Generally, a gene cluster is a group of genes found within a seed's DNA that encode for similar polypeptides, or proteins, which collectively share a generalized function. In FIG. 17, the lower branches or individual end-lines represent different seeds, which are organized in a gene tree according to shared genomic marker data or genes. FIG. 17 illustrates an example where the seeds are further identified by different genetic clusters 1702, 1704, 1706, 1708, 1710. The computer system 130 may receive this genetic cluster data at block 1204, or may use the genomic marker data to organize the seeds into any number of suitable genetic cluster relationships.

Figure 18:
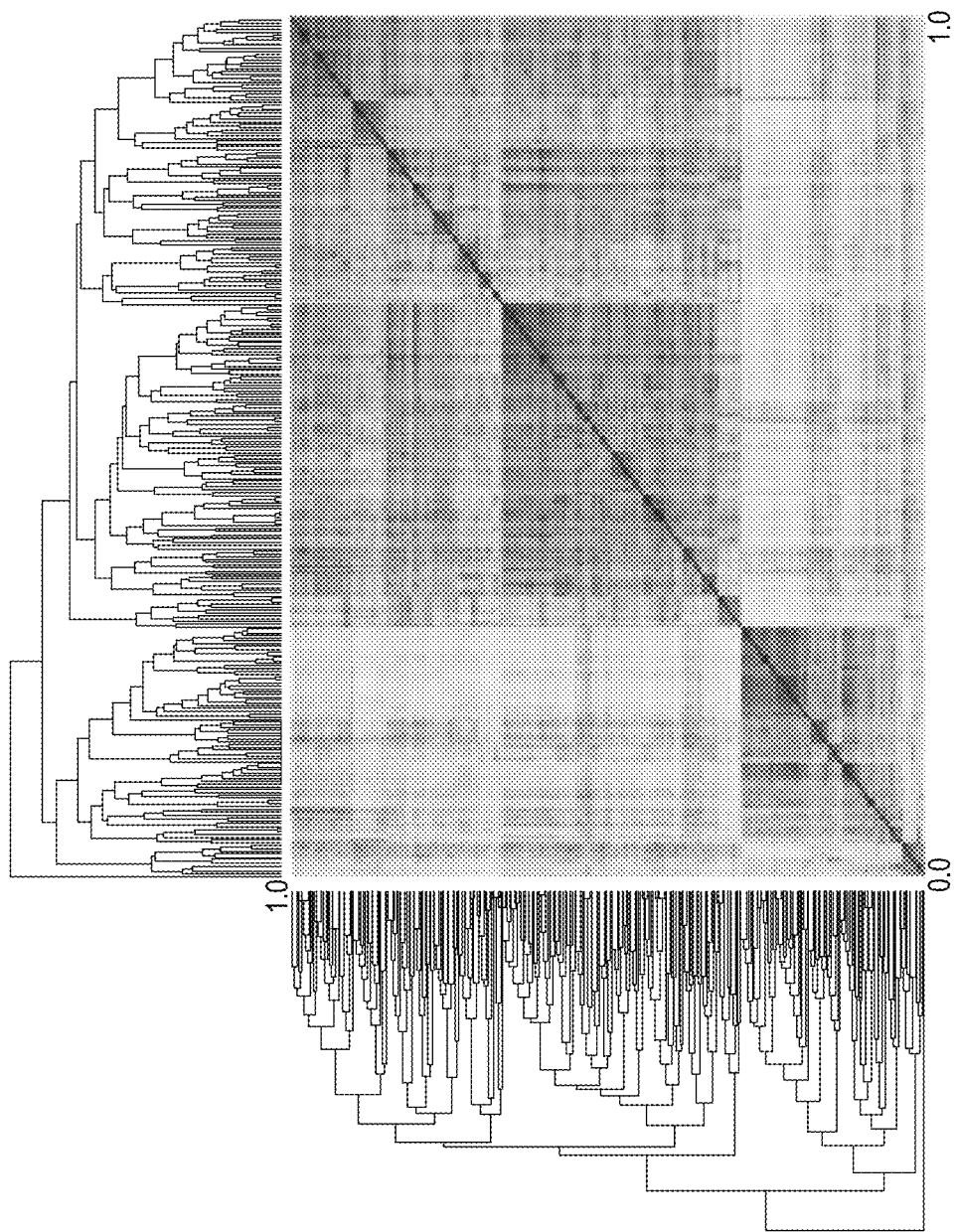
FIG. 18 illustrates an example gene marker-based kinship matrix that identifies pairwise relationships between seeds based on SNP markers.

FIG. 18 illustrates an example gene marker-based kinship matrix that identifies pairwise relationships between seeds based on SNP markers. The relationship is captured by a value between 0.0 and 1.0, wherein a value of 0.0 means that the two seeds are completely different and unrelated according to SNP markers, and a value of 1.0 means that the two seeds are identical. The computer system 130 may receive this marker-based kinship matrix at block 1204, or may use the genomic marker data to generate the matrix using a suitable computation method, such as squared Euclidean distance calculations. As is diagrammatically shown by FIG. 16 and FIG. 18, the marker-based kinship matrix provides more detailed relational data between pairs of seeds as compared to the pedigree-based matrix.

5.2. Data Imputation

At block 1206, the computer system 130 generates predicted yield properties for seeds associated with particular fields or environments. More particularly, the computer system 130 utilizes the received agricultural data records and the genetic feature data, including the genetic relationships between seeds, to provide imputed yield data to fill in the data gaps represented, for instance, in FIG. 13 and FIG. 14. In one example, the computer system uses a statistical mixed effects model to combine various terms in the following mathematical representation: Yield (bu/ac)=f(G+E+G×E+error). The term G represents genetic feature data for the list of hybrids/varieties, and may include relative maturity, biotechnology traits, genomic marker data, a pedigree-based kinship matrix, genetic cluster relationships, and a gene marker-based kinship matrix. The term E represents environmental and management features for a set of fields, and may include precipitation, drought risk, heat stress, soil composition, soil texture, soil drainage, environmental zone, disease risk, crop rotation, tillage practice, and the like. The term G×E is a mathematical term that captures, non-additive interactions between genetic features and environmental/management features. G×E captures variability due to seeds performing differently under different environmental conditions, which may also consider management features. The error term helps to account for yield variations not captured by the G, E, and G×E terms.

Overall, the genetic relationship data, such as the genomic marker data, the pedigree-based kinship matrix, the genetic cluster relationships, and/or the gene marker-based kinship matrix, helps to improve the data imputation process by identifying a degree of genetic similarity between a seed that was tested in particular environmental conditions and a seed that was not tested in the particular environmental conditions. This degree of genetic similarity is used by appropriate machine learning models, such as a statistical mixed effects model or best linear unbiased prediction (BLUP) model, along with genetic features and relationships discussed herein and perhaps others, raw environmental features or filtered and engineered environmental features, and the G×E and/or G×E×M interactions to provide more reliable yield predictions to fill in the data gaps. Each of FIG. 13 and FIG. 14 provides an example of received data records, a processing block 1310, 1410, respectively, using the genetic features, and resulting data records with imputed yield values to fill-in the data gaps.

In one example, imputed yield data can be calculated using a mixed genomic BLUP (GBLUP) model according to an equation: Yield=$X\beta$+$Zu$+error. The $X\beta$ term represents a vector of fixed environmental effects, $Zu$ represents a vector of relationships or correlations between genomic factors and environmental factors, and the error term is a vector of random residual effects to account for other yield variations. In this example, the u term follows a random distribution with correlation captured by a variance-covariance matrix K (e.g., a kinship matrix) and an identify matrix I, and may be determined according to an equation:

$$u \sim N(0, [K \otimes I\sigma_{GE}^2]).$$

5.3. Determine Predicted Yield Performance

At block 1208, the computer system 130 determines predicted yield performance for one or more seeds. In one example, at block 1208, the computer system 130 generates probability of success scores for one or more seeds based on the imputed dataset generated at block 1206, other genetic data, and field attributes for one or more target fields or environments. Alternatively or in combination, the computer system 130 at block 1208 determines the predicted yield performance using the imputed dataset, other genetic data, and field attributes to generate absolute or relative yield values, yield rankings, and/or other yield performance metrics.

In one example, the flowchart 1200 at block 1208 or elsewhere includes receiving or otherwise accessing feature data for the one or more target fields wherein seeds are planned to be planted. Machine learning models are implemented to determine the predicted yield performance for the seeds at the target field(s). In an embodiment, the machine learning models use, as predictor variables, imputed yield data, genetic relationship data, genomic marker data (e.g., data related to FIG. 15), genetic cluster data (e.g., data related FIG. 16 and FIG. 17), and/or genetic kinship matrixes (e.g., matrixes related to FIG. 16 and FIG. 18), G×E features, and environmental and management field attributes. The target variable of the machine learning models may be a probabilistic value ranging from 0 to 1, for example, where 0 equals a 0% probability of a successful yield and 1 equals a 100% probability of a successful yield. In an example, a successful yield is described as the likelihood that the yield of a specific seed is a certain value above the mean yield for similarly classified seeds. For example, a successful yield may be defined as a yield that is 5 bushels per acre above the mean yield of seeds that have the same assigned relative maturity value. Additional details and techniques are described herein in relation to FIG. 7 and FIG. 9, for instance.

5.4 Seed Optimization and Recommendation Generation

At block 1210, the computer system 130 may use unique features or attributes of one or more target fields and the dataset of success probability scores to generate field-specific seed recommendations for the grower's field. The computer system 130 may receive the unique features or attributes of the target fields at block 1210, or may have received these features at some other time. The recommendation may include information such as a seeding rate per density value. The seeding rate per density value may be used to recommend the selection of specific seeds in order to obtain a desired target yield range. In an embodiment, the seeding rate per density may also be used to adjust seed population or seed density. An overall result of the processes of FIG. 12 is that the imputed data provides useful yield information that can be matched to the unique features of the target fields, to thereby customize each recommendation for those unique features. This provides an improvement in average yield over prior models that may generalize recommendations on a larger scale, such as, by region or zip code.

In generating the recommendations, computer system 130 may also perform feature selection to reduce the redundancy from many field features. Generally, feature selection helps to avoid the potential issue of dimensionality, removes redundant features, eliminates non-predictive features or combinations of features, and enhances generalization by reducing overfitting to thereby simplify the models and reduce the impact of missing feature data. The computer system 130 may perform the feature selection using an appropriate strategy, such as automated likelihood-ratio-test-based backward selection.

Further, similarly to other examples discussed herein, the computer system 130 may cause the displaying of the recommendations for each field.

5.5 Validate and Adjust Models

At block 1212, the computer system 130 may validate and adjust the machine learning models. In one example, the validation process includes receiving actual yield data for planted hybrids/varieties in particular fields, and comparing this yield data to the imputed yield data. The validation process may also receive yield data for different seeds grown on the same field, nearby fields, or fields that otherwise share similar combinations of attributes, and compare the yield data for the different seeds against each other. This validation at the field level provides data that can be used to help improve recommendations and yield results over prior models that may perform validation at a regional level. The computer system 130 may then account for discrepancies between the actual and imputed yield data by modifying the corresponding models, such as by modifying the G×E, G×M, and/or G×E×M relationships and/or adjusting the error term discussed above. Future iterations of generating the imputed yield data and planning recommendations may then use the adjusted models.

At block 1212, the computer system 130 may also use the actual yield data along with other data inputs and machine learning techniques to help identify specific environment and management attributes that are predictive of positive seed placement outcomes. Generally, the computer system 130 may apply machine learning techniques to identify correlations between individual attributes and combinations of attributes and yield outcomes. In one example, the predictive attributes are used in future iterations of generating imputed yield data and planning recommendations, for instance, by simplifying calculations and/or data inputs from different users. The predictive attributes may also be used during different breeding and product development stages to help enhance agricultural data and drive research and testing.

Figure 19:
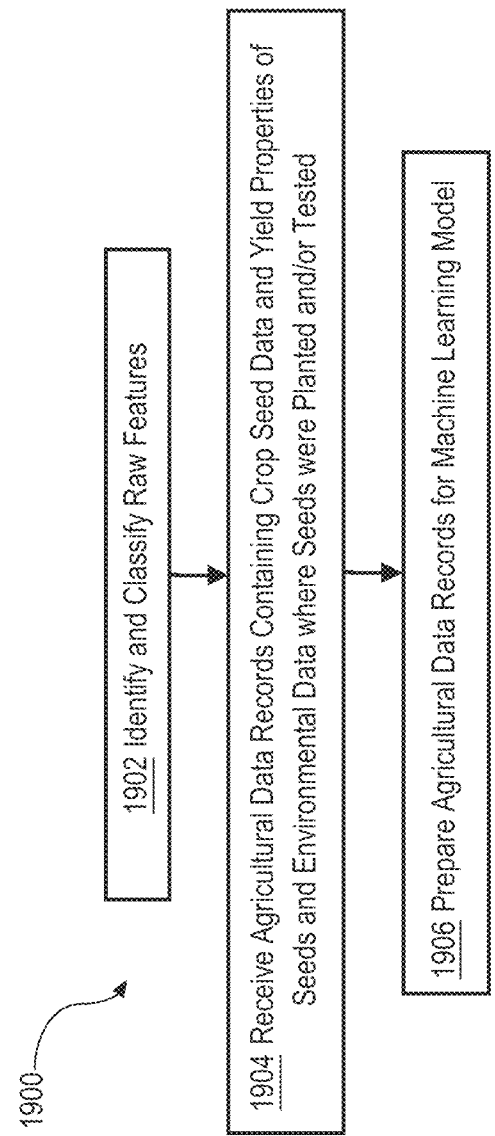
FIG. 19 illustrates an example flowchart that utilizes feature engineering to classify feature data and prepare agricultural data records for the recommendation model of FIG. 12.

6. Functional Overview—Embodiment Including Feature Engineering to Enhance Data for Recommendation Modeling FIG. 19 illustrates an example process of using feature engineering to classify field feature data and prepare agricultural data records for the recommendation model of FIG. 12, for instance. The feature engineering techniques may also be used to enhance a dataset used for the agronomic model training of FIG. 3, for generating and displaying target success yield groups of FIG. 7, and/or for generating and displaying target seeds for planting of FIG. 10.

The processes disclosed herein may be extended and tailored for a particular product, such as corn or soybeans. Between corn and soybean plants, for instance, different environmental and management features may be considered as major drivers in terms of yield for different products. In one embodiment, corn growth is mainly driven by heat units or growing degree units, while day length is a major driver of the onset of the reproductive stage in soybeans. Process 1900 of FIG. 19 may be used to engineer field features for a particular product to leverage knowledge about key features or to otherwise develop and enhance data to provide quality results in recommendation modeling. For instance, engineered features may be used at block 1210 of FIG. 12 to generate field-specific seed recommendations for a target field or environment.

6.1 Raw Features and Feature Classification

At block 1902, the agricultural intelligence computer system 130, for example, identifies raw field features that are significant drivers of yield, and further performs feature classification to transform generally continuous features into categorical features. Raw features include over 130 different features derived from general categories including topography and hydrology, weather, management practices, and soil characteristics. For example, topography and hydrology derived features include elevation, slope, profile curvature (concave/convex characteristics), aspect (compass direction that a slope faces), distance to a water source, soil EC500 measurements, and the like. Weather derived features may relate to day-length, temperature, evapotranspiration, rainfall, solar characteristics, drought indices, among others. Management derived features may include plant timing, harvest timing, planted seeds per acre, seed product segment, seed MAC-zone, seed location maturity group (MG) zones, and others. Soil derived features may quantify or characterize organic matter, textural class, sand/clay percentages, permeability and bulk density, CEC (cation-exchange capacity), PAW (plant available water), and soil productivity index, for example.

At block 1902, the agricultural intelligence computer system 130 identifies, from the over 130 different raw features, a subset of field features that drive yield for a particular product. According to an embodiment, the system 130 transforms otherwise continuous features into categorical features by characterizing at least the identified key features into a smaller number of distinct feature classes or categories. According to an embodiment, at block 1902, the system 130 receives and stores data representing the key feature classifications, for instance, data representing Table 1 provided below. The system 130 may then use such key feature classifications in the recommendation modeling of FIG. 12 to enhance results as compared to using raw continuous features.

Using soybeans as an example, key field features include soil and topography features. Based on field data across different environments (for instance, across the states of Indiana, Illinois, Iowa, Minnesota, Missouri, and Wisconsin) and extensive scientific research, eleven key soil and topographic features may be identified and classified according to the example of Table 1:

TABLE 1

Example Feature Classification

| Feature | Classification criteria | Observations |
|---|---|---|
| pH | 1. High: >7.0;<br>2. Medium: 5.8 to 7.0;<br>3. Low: <5.8 | Optimal range for soybeans 6.0-to-8.0<br>Optimal range for corn 5.5-to-7.5 |
| CEC-cation-exchange capacity [meq/100 mg] | 1. High: >20;<br>2. Medium: 10 to 20;<br>3. Low: <10 | Soils with CEC > 20 meq/100 mg may have high clay content, moderate to high organic matter content, high water holding capacity, less frequent need for lime and fertilizers |
| OM-organic matter | 1. High: >3.5%;<br>2. Medium: 2% to 3.55%;<br>3. Low: <2% | OM of 3-6% is high<br>Crop dry matter yield reduces when OM falls below 2% |
| Soil texture | 1. Clay loam (clay-loam, clay, sandy-clay-loam, sandy clay)<br>2. Loam (loam, sandy-loam, loamy-sand, sand)<br>3. Silty clay loam (silty-clay-loam, silty-clay)<br>4. Silt loam (silt-loam, silt) | |
| Soil drainage | 1. Excess (Excessively drained, Somewhat excessively drained)<br>2. Well (well drained; moderately well drained)<br>3. Poor (somewhat poorly drained, poorly drained, very poorly drained) | Reclassification may or may not account for the presence or absence of tile-drains.<br>Generally, the presence of tile-drains modifies the natural drainage conditions |
| Crop rotation | 1. Corn; Corn-Corn<br>2. Others: Soybean-Corn, Hay-Corn, Wheat-Corn | Using a 1-year rotation, for instance. |
| Tillage | 1. Conventional; Conventional Till<br>2. Others: Conservational No-Till, Conservational Ridge-Till, Conservational Strip-Till, Minimal Till | Fewer fields are under No-Till and other conservational tillage practices |
| Elevation [m] | 1. High: >312;<br>2. Medium: 221 to 312;<br>3. Low: <221 | Based on 3-quantiles (terciles) across IA, IL, IN, MN, MO, WI |
| Slope [degrees] | 1. High: >1.0;<br>2. Medium: 0.4 to 1.0;<br>3. Low: <0.4 | Based on 3-quantiles (terciles) across IA, IL, IN, MN, MO, WI |
| Aspect [degrees] | 1. Class 1: >234;<br>2. Class 2: 120 to 234;<br>3. Class 3: <120 | Based on 3-quantiles (terciles) across IA, IL, IN, MN, MO, WI |
| Profile curvature | 1. Class 1: >0.0001<br>2. Class 2: −0.0001 to 0.0001<br>3. Class 3: <−0.0001 | Based on 3-quantiles (terciles) across IA, IL, IN, MN, MO, WI |

6.2 Prepare Data

At block 1904, the agricultural intelligence computer system 130, for example, receives agricultural data records over a digital data communication network 109. The agricultural data records include, for instance, crop seed data and yield properties of seeds and field data (e.g., environmental feature data) where the seeds were planted and/or tested. At block 1906, the system 130 further prepares the received agricultural data records for a machine learning model, for instance, the recommendation model of FIG. 12. According to an embodiment, the system 130 uses the key feature classifications of block 1902 to characterize received field data, such as the environmental feature data, in preparation for use in a machine learning model. More particularly, the system 130 transforms or characterizes the raw field feature data into distinct feature classes using distinct feature classifications from block 1902, such as the classification criteria of Table 1. Illustratively, as a result of blocks 1904 and 1906, the system 130 associates yield properties of seeds from a plurality of fields with key feature classifications corresponding to the specific field conditions.

At block 1906, the system 130 may also perform filtering to extract more significant data for use in recommendation modeling. In the context of soybeans, significant yield data may be found in relation to fields with multiple products tested or grown in that same field, as opposed to fields with only a single or a relatively small number of products. For instance, at block 1906, the system 130 may extract or identify agricultural data records for only fields with six or more products tested concurrently, and prepare distinctly only this extracted data using key feature classifications for recommendation modeling.

According to an embodiment, the system 130 uses the processed agricultural data records to generate G×E relationships between genetic features of seeds, field features, and yield properties using, for instance, some form of a BLUP model (e.g., an environmental best linear unbiased prediction (eBLUP) model), T-stat, and/or a kernel smoothing using a Gaussian process. The system 130 may also use the processed agricultural data to fill-in data gaps according to block 1206 of FIG. 12, for example. As discussed above in relation to blocks 1206, 1208, and 1210, for instance, the system 130 is configured to use the G×E relationships and/or imputed data to generate predicted yield performance for one or more seeds and one or more specific target fields with particular field conditions or features, and from the predicted yield performance, to generate field-level yield improvement product recommendations. Such recommendations include seed, hybrid, and/or variety recommendations for the target fields, which when implemented help to improve actual yield performance. To facilitate implementation of the product recommendations and improve resulting yield, the system 130 is further configured to cause display of the product recommendations on a display device communicatively coupled to the system. A grower may select or confirm a product recommendation and instruct the system 130 to control one or more machines to implement the product recommendation.

In practice, the feature engineering techniques disclosed herein have been used to prepare data from thousands fields, many of which include a plurality of products grown thereon (e.g., six or more soybean varieties), to develop data for thousands of products (e.g., nearly 3000 soybean varieties). Resulting engineered feature data and genomic-by-environmental relationships have been used to provide product recommendations resulting in statistically significant lift over other models. For instance, using feature engineering techniques to develop product recommendations for specific, target fields, has provided a greater than 0.8 bpa (bushels per acre) increase over product recommendations on a regional basis that do not use the present feature engineering techniques.

What is claimed is:

1. A computer-implemented method comprising:
receiving, by a server computer system, a plurality of agricultural data records, wherein a representative agricultural data record of the plurality of agricultural data records comprises a yield property of one or more products grown in a given field and continuous data indicative of multiple raw field features and specific to the given field, the multiple raw field features including pH, soil cation-exchange capacity (CEC), and organic matter (OM);
identifying a subset of the agricultural data records corresponding to one or more fields with a plurality of products grown concurrently;
transforming, by the server computer system, the continuous data in the subset of the agricultural data records into distinct feature classes;
generating, by the server computer system, using the plurality of agricultural data records, the distinct feature classes, and one or more of a best linear unbiased prediction model, a T-stat, or kernel smoothing using a Gaussian process, genomic-by-environmental relationships between the one or more products, yield properties of the one or more products, and field features associated with the one or more products;
generating, by the server computer system, based at least in part on the genomic-by-environmental relationships, using a statistical mixed effects model, predicted yield performance for a set of products associated with one or more target environments;
generating, using the server computer system, product recommendations for the one or more target environments based on the predicted yield performance for the set of products; and
providing one or more instructions configured to cause display, on a display device communicatively coupled to the server computer system, of the product recommendations.

2. The method of claim 1, wherein generating the genomic-by-environmental relationships includes using the best linear unbiased prediction model.

3. The method of claim 1, wherein the product recommendations are for soybean varieties.

4. The method of claim 1, wherein the multiple raw field features further include one or more of soil texture, soil drainage, crop rotation, tillage, field elevation, and/or field slope.

5. The method of claim 1, wherein the distinct feature classes include:
for the pH, a high pH range greater than 7.0, a medium pH range between 5.8 and 7.0, and a low pH range less than 5.8; and
for the soil CEC, a high CEC range greater than 20, a medium CEC range between 10 and 20, and a low CEC range less than 10.

6. One or more non-transitory computer-readable storage media storing instructions which when executed by one or more processors cause performing operations comprising:
receiving a plurality of agricultural data records, wherein a representative agricultural data record of the plurality of agricultural data records comprises a yield property of one or more products grown in a given field and continuous data indicative of multiple raw field features and specific to the given field, the multiple raw field features including pH, soil cation-exchange capacity (CEC), and organic matter (OM);
identifying a subset of the agricultural data records corresponding to one or more fields with a plurality of products grown concurrently;
transforming the continuous data in the subset of the agricultural data records into distinct feature classes;
generating, using the plurality of agricultural data records, the distinct feature classes, and one or more of a best linear unbiased prediction model, a T-stat, or kernel smoothing using a Gaussian process, genomic-by-environmental relationships between the one or more products, yield properties of the one or more products, and field features associated with the one or more products;
generating, based at least in part on the genomic-by-environmental relationships, using a statistical mixed effects model, predicted yield performance for a set of products associated with one or more target environments;
generating product recommendations for the one or more target environments based on the predicted yield performance for the set of products; and
providing one or more instructions configured to cause display, on a display device communicatively coupled to one or more processors, of the product recommendations.

7. The one or more non-transitory computer-readable storage media of claim 6, wherein the operation of generating the genomic-by-environmental relationships includes using the best linear unbiased prediction model.

8. The one or more non-transitory computer-readable storage media of claim 6, wherein the product recommendations are for soybean varieties.

9. The one or more non-transitory computer-readable storage media of claim 6, wherein the one or more products include soybean varieties.

10. The one or more non-transitory computer-readable storage media of claim 9, wherein the multiple raw field features further include one or more of soil texture, soil drainage, crop rotation, tillage, field elevation, and/or field slope.

11. The one or more non-transitory computer-readable storage media of claim 6, wherein the distinct feature classes include:
for the pH, a high pH range greater than 7.0, a medium pH range between 5.8 and 7.0, and a low pH range less than 5.8; and
for the soil CEC, a high CEC range greater than 20, a medium CEC range between 10 and 20, and a low CEC range less than 10.

* * * * *